(12) United States Patent
Eminoglu et al.

(10) Patent No.: US 10,619,172 B2
(45) Date of Patent: Apr. 14, 2020

(54) INCREASED ETHANOL PRODUCTION BY THERMOPHILIC MICROORGANISMS WITH DELETION OF INDIVIDUAL HFS HYDROGENASE SUBUNITS

(71) Applicant: THE TRUSTEES OF DARTMOUTH COLLEGE, Hanover, NH (US)

(72) Inventors: Aysenur Eminoglu, Hanover, NH (US); Daniel G. Olson, Hanover, NH (US); Lee R. Lynd, Plainfield, NH (US)

(73) Assignee: THE TRUSTEES OF DARTMOUTH COLLEGE, Hanover, NH (US)

( * ) Notice: Subject to any disclaimer, the term of this patent is extended or adjusted under 35 U.S.C. 154(b) by 124 days.

(21) Appl. No.: 15/656,665

(22) Filed: Jul. 21, 2017

(65) Prior Publication Data
US 2018/0023100 A1 Jan. 25, 2018

Related U.S. Application Data

(60) Provisional application No. 62/365,200, filed on Jul. 21, 2016.

(51) Int. Cl.
| | | |
|---|---|---|
| C12N 9/02 | (2006.01) | |
| C12P 7/06 | (2006.01) | |
| C12N 1/20 | (2006.01) | |
| C12N 15/00 | (2006.01) | |
| C12Q 1/68 | (2018.01) | |
| C07H 21/04 | (2006.01) | |

(52) U.S. Cl.
CPC ............ *C12P 7/065* (2013.01); *C12N 1/20* (2013.01); *C12N 9/0067* (2013.01); *C12N 15/00* (2013.01); *C12Y 112/07002* (2013.01); *Y02E 50/17* (2013.01)

(58) Field of Classification Search
None
See application file for complete search history.

(56) References Cited

U.S. PATENT DOCUMENTS

2011/0256601 A1* 10/2011 Shaw, IV ............ C12N 9/0006
435/165

OTHER PUBLICATIONS

Eminoglu. Deletion of the hfsB gene increases ethanol production in Thermoanaerobacterium saccharolyticum and several other thermophilic anaerobic bacteria. Biotechnology for Biofuels. 2017. 10:282.*
Altschul et al. (1990) "Basic local alignment search tool." J. Mol. Biol., 215, pp. 403-410.
Amador-Noguez et al. (2010) "Systems-level metabolic flux profiling elucidates a complete, bifurcated tricarboxylic acid cycle in Clostridium acetobutylicum." J. Bacteriol., 192, pp. 4452-4461.
Argyros et al. (2011) "High ethanol titers from cellulose by using metabolically engineered thermophilic, anaerobic microbes." Appl. Environ. Microbial., 77, pp. 8288-8294.

(Continued)

*Primary Examiner* — Yong D Pak
(74) *Attorney, Agent, or Firm* — Lathrop GPM LLP

(57) ABSTRACT

Disclosed are methods for engineering bacteria, for example, *Thermoanaerobacterium saccharolyticum*, that convert biomass to ethanol at high yield by deleting a single gene. Deletion of subunit A or subunit B of the hfs hydrogenase, but not deletion of subunit C or subunit D, results in an increase in ethanol yield.

12 Claims, 7 Drawing Sheets
Specification includes a Sequence Listing.

(56) References Cited

OTHER PUBLICATIONS

Arnau et al. (1998) "Cloning of the Lactococcus lactis adhE gene, encoding a multifunctional alcohol dehydrogenase, by complementation of a fermentative mutant of *Escherichia coli*." J. Bacteriol, 180, pp. 3049-3055.

Atteia et al. (2003) "Bifunctional aldehyde/alcohol dehydrogenase (ADHE) in chlorophyte algal mitochondria." Plant Mol. Biol., 53, pp. 175-188.

Bertani (1951) "Studies on lysogenesis. I. The mode of phage liberation by lysogenic *Escherichia coli*." J. Bacteriol., 62, pp. 293-300.

Bhandiwad et al. (2014) "Metabolic engineering of Thermoanaerobacterium saccharolyticum for nbutanol production." Metab. Eng., 21, pp. 17-25.

Biswas et al. (2015) "Elimination of hydrogenase active site assembly blocks H2 production and increases ethanol yield in Clostridium thermocellum." Biotechnol. Biofuels, 8, p. 20.

Blumer-Schuette et al. (2014) "Thermophilic lignocellulose deconstruction." FEMS Microbial. Rev., 38, pp. 393-448.

Boxma et al. (2004) "The anaerobic chytridiomycete fungus *Piromyces* sp. E2 produces ethanol via pyruvate:formate lyase and an alcohol dehydrogenase." E. Mol. Microbial., 51, pp. 1389-1399.

Brown et al. (2011) "Mutant alcohol dehydrogenase leads to improved ethanol tolerance in Clostridium thermocellum." Proc. Natl. Acad. Sci., 108, pp. 13752-13757.

Bryant et al. (1988) "Purification and Properties of Primary and Secondary Alcohol Dehydrogenases from Thermoanaerobacter ethanolicus." Appl. Environ. Microbial., 54, pp. 460-465.

Buckel et al. (2013) "Energy conservation via electron bifurcating ferredoxin reduction and proton/Na(+) translocating ferredoxin oxidation." Biochim. Biophys. Acta, 1827, pp. 94-113.

Burdette et al. (1994) "Purification of acetaldehyde dehydrogenase and alcohol dehydrogenases from Thermoanaerobacter ethanolicus 39E and characterization of the secondary-alcohol dehydrogenase (2 degrees Adh) as a bifunctional alcohol dehydrogenase-acetyl-CoA reductive thioest." Biochem. J., 302, pp. 163-170.

Carere et al. (2012) "Linking genome content to biofuel production yields: a meta-analysis of major catabolic pathways among select H2 and ethanol-producing bacteria." BMC Microbial., 12, p. 295.

Chabriere et al. (2011) "Pyruvateferredoxin oxidoreductase." Encyclopedia of Inorganic and Bioinorganic Chemistry, pp. 1-13.

Chen et al. (1991) "Role of aspartic acid 38 in the cofactor specificity of *Drosophila* alcohol dehydrogenase." Eur. J. Biochem., 202, pp. 263-267.

Chen et al. (2004) "Structural analysis of the acetaldehyde dehydrogenase activity of Entamoeba histolytica alcohol dehydrogenase 2 (EhADH2), a member of the ADHE enzyme family." Mol. Biochem. Parasitol., 137, pp. 201-210.

Cronan et al. (2005) "Function, Attachment and Synthesis of Lipoic Acid in *Escherichia coli*." vol. 50. Elsevier Masson SAS, 44 pp.

Currie et al. (2013) "Functional heterologous expression of an engineered full length CipA from Clostridium thermocellum in Thermoanaerobacterium saccharolyticum." Biotechnol. Biofuels, 6, p. 32.

Currie et al. (2014) "Profile of secreted hydrolases, associated proteins, and SlpA in Thermoanaerobacterium saccharolyticum during the degradation of hemicellulose." Appl. Environ. Microbial., 80, pp. 5001-5011.

Desai et al. (2004) "Cloning of L-lactate dehydrogenase and elimination of lactic acid production via gene knockout in Thermoanaerobacterium saccharolyticum JW/SL-YS485." Appl. Micro. Biol. Biotechnol., 65, pp. 600-605.

Eram et al. (2014) "The bifunctional pyruvate decarboxylase/pyruvate ferredoxin oxidoreductase from Thermococcus guaymasensis." Archaea, pp. 349-379.

Espinosa et al. (2001) "The bifunctional Entamoeba histolytica alcohol dehydrogenase 2 (EhADH2) protein is necessary for amebic growth and survival and requires an intact C-terminal domain for both alcohol dehydrogenase and acetaldehyde dehydrogenase activity." J. Biol. Chem., 276, pp. 20136-20143.

Extance et al. (2013) "Structure of a bifunctional alcohol dehydrogenase involved in bioethanol generation in Geobacillus thermoglucosidasius." Acta Crystallogr. Sect. D Biol. Crystallogr., 69, pp. 2104-2115.

Fournier et al. (2004) "A new function of the Desulfovibrio vulgaris Hildenborough [Fe] hydrogenase in the protection against oxidative stress." J. Biol. Chem., 279, pp. 1787-1793.

Herring et al. (2012) "Final Report on Development of Thermoanaerobacterium Saccharolyticum for the Conversion of Lignocellulose to Ethanol." Golden, CO (United States), 17 pp.

Hogsett (1995) "Cellulose hydrolysis and fermentation by Clostridium thermocellum for the production of ethanol." Dartmouth College, Hanover, NH, 366 pp.

Huang et al. (2012) "Electron bifurcation involved in the energy metabolism of the acetogenic bacterium Moorella thermoacetica growing on glucose or H2 plus CO2." J. Bacteriol., 194, pp. 3689-3699.

Jo et al. (2008) "Software news and updates CHARMMGUI: A web-based graphical user interface for CHARMM." J. Comput. Chem., 29, pp. 1859-1865.

Jorgensen et al. (1983) "Comparison of simple potential functions for simulating liquid water." J. Chem. Phys., 79, pp. 926-935.

Kanehisa et al. (2000) "KEGG." Kyoto Encyclopedia of Genes and Genomes, 28, pp. 27-30.

Kanehisa et al. (2014) "Data, information, knowledge and principle: back to metabolism in KEGG." Nucleic Acids Res., 42 (Database issue), pp. DI99-D205.

Kessler et al. (1992) "Ultrastructure and pyruvate formate-lyase radical quenching property of the multienzymic AdhE protein of *Escherichia coli*." J. Biol. Chem., 267, pp. 18073-18083.

Konig (1998) "Subunit structure, function and organisation of pyruvate decarboxylases from various organisms." Biochim. Biophys. Acta, 1385, pp. 271-286.

Koo et al. (2005) "Cloning and characterization of the bifunctional alcohol/acetaldehyde dehydrogenase gene (adhE) in Leuconostoc mesenteroides isolated from kimchi." Biotechnol. Lett., 27, pp. 505-510.

Koukos et al. (2013) "Grcarma: A fully automated task-oriented interface for the analysis of molecular dynamics trajectories." J. Comput. Chem., 34, pp. 2310-2312.

Kruger (1994) "The Bradford method for protein quantitation." Methods Mol. Biol., 32, pp. 9-15.

Lamed et al. (1980) Ethanol production by thermophilic bacteria: relationship between fermentation product yields of and catabolic enzyme activities in Clostridium thermocellum and Thermoanaerobium brockii. J. Bacteriol., 144, pp. 569-578.

Lee et al. (1993) "Taxonomic Distinction of Saccharolytic Thermophilic Anaerobes: Description *of Thermoanaerobacterium xylanolyticum* gen. nov., sp. nov., and *Thermoanaerobacterium saccharolyticum* gen. nov., sp. nov.; Reclassification of Thermoanaerobium brock:ii, Clostridium." Int J Syst Bacteriol, 43, pp. 41-51.

Lee et al. (2011) "Detoxification of woody hydrolyzates with activated carbon for bioconversion to ethanol by the thermophilic anaerobic bacterium Thermoanaerobacterium saccharolyticum." Biomass and Bioenergy, 35, pp. 626-636.

Lo et al. (2015) The bifunctional alcohol and aldehyde dehydrogenase gene, adhE, is necessary for ethanol production in Clostridium thermocellum and Thermoanaerobacterium saccharolyticum. J. Bacterial, 197, pp. 1386-1393.

Lovitt et al. (1984) "Ethanol Production by Thermophilic Bacteria: Physiological Comparison of Solvent Effects on Parent and Alcohol Tolerant Strains of Clostridium thermohydrosulfuricum." Appl. Envir. Microbial., 48, pp. 171-177.

Lovitt et al. (1988) "Ethanol production by thermophilic bacteria: biochemical basis for ethanol and hydrogen tolerance in Clostridium thermohydrosulfuricum." J. Bacterial, 170, pp. 2809-2815.

Lynd et al. (2002) "Microbial cellulose utilization: fundamentals and biotechnology." Microbial. Mol. Biol. Rev., 66, pp. 506-577.

Lynd et al. (2005) "Consolidated bioprocessing of cellulosic biomass: an update." Curr. Opin. Biotechnol., 16, pp. 577-583.

Ma et al. (1997) "Pyruvate ferredoxin oxidoreductase from the hyperthermophilic archaeon, Pyrococcus furiosus, functions as a CoA-dependent pyruvate decarboxylase." Proc. Natl. Acad. Sci. USA, 94, pp. 9608-9613.

(56) References Cited

OTHER PUBLICATIONS

Ma et al. (2001) "Ferredoxin:NADP oxidoreductase from Pyrococcus furiosus." Methods in Enzymology, vol. 334, pp. 40-45.

Mai et al. (1997) "Transformation of *Thermoanaerobacterium* sp. strain JW/SL-Y5485 with plasmid pIKMI conferring kanamycin resistance." FEMS Microbial. Lett., 148, pp. 163-167.

Membrillo-Herna et al. (2000) "Evolution of the adhE gene product of *Escherichia coli* from a functional reductase to a dehydrogenase." J. Biol. Chem., 275, pp. 33869-33875.

Montella et al. (2005) "Crystal structure of an iron-dependent group III dehydrogenase that interconverts L-lactaldehyde and L-1,2-propanediol in *Escherichia coli.*" J. Bacterial., 187, pp. 4957-4966.

Neale et al. (1986) "The two alcohol dehydrogenases of Zymomonas mobilis purification by differential dye ligand chromatography, molecular characterisation and physiological roles." Eur. J. Biochem., 154, pp. 119-124.

Olson et al. (2012) "Computational design and characterization of a temperature-sensitive plasmid replicon for gram positive thermophiles." J. Biol. Eng., 6, p. 5.

Olson et al. (2012) "Recent progress in consolidated bioprocessing." Curr. Opin. Biotechnol., 23, pp. 396-405.

Olson et al. (2012) "Transformation of Clostridium thermocellum by electroporation.Methods in Enzymology," Methods in Enzymology, vol. 510, 14 pp.

Pei et al. (2010) "*Thermoanaerobacter* spp. control ethanol pathway via transcriptional regulation and versatility of key enzymes." Metab. Eng., 12, pp. 420-428.

Peng et al. (2008) "The aldehyde/alcohol dehydrogenase (AdhE) in relation to the ethanol formation in Thermoanaerobacter ethanolicus JW200." Anaerobe, 14, pp. 125-127.

Pineda et al. (2013) "The bifunctional aldehyde-alcohol dehydrogenase controls ethanol and acetate production in Entamoeba histolytica under aerobic conditions." FEBS Lett., 587, pp. 178-184.

Podkaminer et al. (2012) "Characterization of xylan utilization and discovery of a new endoxylanase in Thermoanaerobacterium saccharolyticum through targeted gene deletions." Appl. Environ. Microbiol., 78, pp. 8441-8447.

Radianingtyas et al. (2003) "Alcohol dehydrogenases from thermophilic and hyperthermophilic archaea and bacteria." FEMS Microbial. Rev., 27, pp. 593-616.

Sato et al. (1993) "Characterization of and ethanol hyper-production by Clostridium thermocellum I-1-B." Biosci. Biotechnol. Biochem., 57, pp. 2116-2121.

Schwarzenbacher et al. 2004 Crystal structure of an iron-containing 1,3-propanediol dehydrogenase (TM0920) from Thermotoga maritima at 1.3 A resolution. Proteins Struct. Funct. Bioinforma., 54, pp. 174-177.

Shanks et al. (2006) "*Saccharomyces cerevisiae*-based molecular tool kit for manipulation of genes from gram-negative bacteria." Appl. Environ. Microbial., 72, pp. 5027-5036.

Shao et al. (2011) "Mutant selection and phenotypic and genetic characterization of ethanoltolerant strains of Clostridium thermocellum." Appl. Microbial. Biotechnol., 92, pp. 641-652.

Shaw et al. (2008) "End-product pathways in the xylose fermenting bacterium, Thermoanaerobacterium saccharolyticum." Enzyme Microb. Technol., 42, pp. 453-458.

Shaw et al. (2008) Metabolic engineering of a thermophilic bacterium to produce ethanol at high yield. Proc. Natl. Acad. Sci. U. S. A., 105, pp. 13769-13774.

Shaw et al. (2009) "Identification of the [FeFe]-Hydrogenase Responsible for Hydrogen Generation in Thermoanaerobacterium Saccharolyticum and Demonstration of Increased Ethanol Yield via Hydrogenase Knockout." Journal of Bacteriology, 191, 20, pp. 6457-6464.

Shaw et al. (2010) "Natural competence in *Thermoanaerobacter* and *Thermoanaerobacterium* species." Appl. Environ. Microbial., 76, pp. 4713-4719.

Shaw et al. (2011) "Marker removal system for Thermoanaerobacterium saccharolyticum and development of a markerless ethanologen." Appl. Environ. Microbial., 77, pp. 2534-2536.

Shaw et al. (2012) "Urease expression in a Thermoanaerobacterium saccharolyticum ethanologen allows high titer ethanol production." Metab. Eng., 14, pp. 528-532.

Shaw et al. (2015) "Anaerobic Detoxification of Acetic Acid in a Thermophilic Ethanologen." Biotechnology for Biofuels, 8, p. 75.

Soboh et al. (2004) "A multisubunit membrane-bound [NiFe] hydrogenase and an NADH-dependent Fe-only hydrogenase in the fermenting bacterium Thermoanaerobacter tengcongensis." Microbiology, 150, pp. 2451-2463.

Sudha et al. (1996) "Improved ethanol tolerance and production in strains of Clostridium thermocellum." World J. Microbial. Biotechnol., 12, pp. 57-60.

Thauer et al. (1972) "Properties and Function of the Pyruvate-Formate-Lyase Reaction in Clostridiae." Eur. J. Biochem., 27, pp. 282-290.

Thorsness et al. (1987) "Inactivation of isocitrate dehydrogenase by phosphorylation is mediated by the negative charge of the phosphate." J. Biol. Chem., 262, pp. 10422-10425.

Tripathi et al. (2010) "Development of pyrF-based genetic system for targeted gene deletion in Clostridium thermocellum and creation of a pta mutant." Appl. Environ. Microbial., 76, pp. 6591-6599.

Van der Veen et al. (2013) "Characterization of Clostridium thermocellum strains with disrupted fermentation end-product pathways." J. Ind. Microbial. Biotechnol., 40, pp. 725-734.

Verbeke et al. (2013) "Genomic evaluation of *Thermoanaerobacter* spp. for the construction of designer co-cultures to improve lignocellulosic biofuel production." PLoS One, 8, pp. 1-18.

Wang et al. (2010) "NADP+ reduction with reduced ferredoxin and NADP+ reduction with NADH are coupled via an electronbifurcating enzyme complex in Clostridium kluyveri." J. Bacterial., 192, pp. 5115-5123.

Wiegel et al. (1981) "*Thermoanaerobacter ethanolicus* gen. nov., spec. nov., a new, extreme thermophilic, anaerobic bacterium." Arch. Microbial., 128, pp. 343-348.

Wigley et al. (1992) "Structure of a ternary complex of an allosteric lactate dehydrogenase from Bacillus stearothermophilus at 2.5 A resolution." J. Mol. Biol., 223, pp. 317-335.

Williams et al. (2007) "Proteomic profile changes in membranes of ethanol-tolerant Clostridium thermocellum." Appl. Microbial. Biotechnol., 74, pp. 422-432.

Wyman (2007) "What is (and is not) vital to advancing cellulosic ethanol." Trends Biotechnol., 25, pp. 153-157.

Yao (2008) Ph.D. thesis. Technical University of Denmark, Denmark, 106 pages.

Yao et al. (2010) "Identification and overexpression of a bifunctional aldehyde/alcohol dehydrogenase responsible for ethanol production in Thermoanaerobacter mathranii." J. Mol. Microbiol. Biotechnol., 19, pp. 123-133.

Yao et al. (2010) Metabolic engineering to improve ethanol production in Thermoanaerobacter mathranii. Appl. Microbial. Biotechnol., 88, pp. 199-208.

Zhang et al. (2003) "Quantification of cell and cellulase mass concentrations during anaerobic cellulose fermentation : development of an enzyme-linked immunosorbent assay-based method with application to Clostridium thermocellum batch cultures." Anal. Chem., 75, pp. 3131-3139.

Zhang et al. (2005) "Regulation of cellulase synthesis in batch and continuous cultures of Clostridium thermocellum." J. Bacteriol., 187, pp. 99-106.

Zhou et al. (2013) "Atypical glycolysis in Clostridium thermocellum." Appl. Environ. Microbial., 79, pp. 3000-3008.

\* cited by examiner

Figure 5A

Amino acid sequence of *Thermoanaerobacterium saccharolyticum hfsA*

MVITVCVGSSCHLKGSYDVINKLKEMIKNYGIEDKVELKADFCMGNCLRAVSVKIDGGACLSIKPNSVERFFKE
HVLGELK (SEQ *ID* No. 1)

Amino acid sequence of *Thermoanaerobacterium saccharolyticum hfsB*

MSVINFKEANCRNCYKCIRYCPVKAIKVNDEQAEIIEYRCIACGRCLNICPQNAKTVRSDVERVQSFLNKGEKV
AFTVAPSYPALVGHDGALNFLKALKSLGAEMIVETSVGAMLISKEYERYYNDLKYDNLITTSCPSVNYLVEKYYP
DLIKCLVPVVSPMVAVGRAIKNIHGEGVKVVFIGPCLAKKAEMSDFSCEGAIDAVLTFEEVMNLFNTNKIGVE
CTKENLEDVDSESRFKLYPIEGKTMDCMDVDLNLRKFISVSSIENVKDILNDLRAGNLHGYWIEANACDGGCI
NGPAFGKLESGIAKRKEEVISYSRMKERFSGDFSGITDFSLDLSRKFIDLSDRWKMPSEMEIKEILSKIGKFSVED
ELNCGACGYDTCREKAIAVFNGMAEPYMCLPYMRGRAETLSNIIISSTPNAIIAVNNEYEIQDMNRAFEKMFL
VNSAMVKGEDLSLIFDISDFVEVIENKKSIFNKKVSFKNYGIIALESIYYLEEYKIAIGIFTDITKMEKQKESFSKLKR
ENYQLAQQVIDRQMKVAQEIASLLGETTAETKVILTKMKDMLLNQGDDE (SEQ *ID* No. 4)

Amino acid sequence of *Thermoanaerobacterium saccharolyticum hfsC*

MSHYIDIAHASLNKYDEELCGDSVQIIRKKDYAMAVMADGLGSGVKANILSTLTTRIVSKMLDMGSELRDVV
ETVAETLPICKERNIAYSTFTVVSIYGDNAHLVEYDNPSVFYFKNGVHKKVDRKCVEIGDKKIFESSFKLDLNDA
LIVVSDGVIHAGVGGILNLGWQWDNVKQYLSKVLEVYSDASDICSQLITTCNNLYKNRPGDDTTAIVIKVNES
KKVTVMVGPPILKNMDEWVVKKLMKSEGLKVVCGGTAAKIVSRILNKDVITSTEYIDPDIPPYAHIDGIDLVTE
GVLTLRKTVEIFKEYMNDKDSNLLRFSKKDAATRLFKILNYATDVNFLVGQAVNSAHQNPDFPSDLRIKVRIVE
ELISLLERLNKNVEVNYF (SEQ *ID* No. 7)

Amino acid sequence of *Thermoanaerobacterium saccharolyticum hfsD*

LFKFNTDVQMLKYEVLYNVAKLTLEDRLEDEYDEIPYEIIPGTKPRFRCCVYKERAIIEQRTKVAMGKNLKRTM
KHAVDGEEPIIQVLDIACEECPIKRYRVTEACRGCITHRCTEVCPKGAITIINKKANIDYDKCIECGRCKDACPYN
AISDNLRPCIRSCSAKAITMDEELKAAINYEKCTSCGACTLACPFGAITDKSYIVDIIRAIKSGKKVYALVAPAIAS
QFKDVTVGQIKSALKEFGFVDVIEVALGADFVAMEEAKEFSHKIKDIKVMTSSCCPAFVAHIKKSYPELSQNIST
TVSPMTAISKYIKKHDPMAVTVFIGPCTAKKSEVMRDDVKGITDFAMTFEEMVAVLDAAKIDMKEQQDVEV
DDATLFGRKFARSGGVLEAVVEAVKEIGADVEVNPVVCNGLDECNKTLKIMKAGKLPNNFIEGMACIGGCIG
GAGVINNNVNQAKLAVNKFGDSSYHKSIKDRISQFDTDDVDFHVDSGEDESSETSFKEA (SEQ *ID* No. 8)

Figure 5B

Amino acid sequence of *Thermoanaerobacterium thermosaccharolyticum hfsA*

MVITVCVGSSCHLKGSYDVINELKKFIKDYNLEDRVELKADFCMGNCLRAVSVKIDDGKCLSIKPNNVEKFFRE
YVLGNLQ (SEQ ID No. 2)

Amino acid sequence of *Thermoanaerobacterium thermosaccharolyticum hfsB*

MSVINFKEANCRNCYKCIRYCPVKAIKVNNEQAEIVDYMCIACGRCLNVCPQNAKTVRSDIEKVKAFIKKGDK
VVFTIAPSYPALVGSGRAFKFLNALKSLGAEMIIETSVGAMFISKEYERYYNDLKYDNLITTSCPSINYLIEKYYPD
LINCLVPVVSPMIAVGRVVKKVYGNEIKVVFIGPCLAKKVEMNDFSCEDAIDAVLTFEEIIEWLDGDGINIDSRE
EFTDCVDTMMPFKLYPIEGKTIDCMDVDLNLRKVVSVSSIDNVKDLLNDIRSGNLHGYWIEANACDGGCING
PAFGRSNSGVVKRKEEVINYSNTKANFINDISNMIDCSVDFTRKFINLSDKWKMPSENEIKNILSKIGKFTKEDE
LNCGACGYDTCREKAIAVFNGMAEPYMCLPYMRGRAETLSNIIISSTPNAIIAVNNEYEIQDMNRAFEKMFLV
NSTMVKNENLSLIFDISDFKDVIENKKSIFNKKVSFKNYGIIALESIYYLEEYKIAIGIFTDITKMEKQKEAFSKVKR
ENYQLAQQVIDRQMKVAQEIASLLGETTAETKVILTRMKDMLLNQGDDE (SEQ ID No. 5)

Amino acid sequence of *Thermoanaerobacterium xylanolyticum hfsA*

MVITVCVGSSCHLKGSYDVINKLKEMIKNYGIEDKVELKADFCMGNCLRAVSVKIDDGKCLSVKPNNVEKFFK
EYVLGELK (SEQ ID No. 3)

Amino acid sequence of *Thermoanaerobacterium xylanolyticum hfsB*

MSVINFKEANCRNCYKCIRYCPVKAIKVNNEQAEIIEYRCIACGRCLNICPQNAKTVRSDVEIVQSFLNRGEKV
VFTVAPSYPALVGHNNALKFLKALKSLGAEMIVETSVGAMLISKEYEKYYNDLKYDNLITTSCPSVNYLVEKYYP
DLINCLVPVVSPMVAVGRAIKIMYGESMKVVFIGPCLAKKAEMNDFSCEGAIDAVLTFEEVMNLLGTDEVDF
EYMEDYLEDVDVEEQYKLYPIEGKTIDCMDVDLNLRKVVSVSSIENVKDLLNDLRYGNLHGYWIEANACDGG
CINGPAFGKLKSGIAKRKEEVISYSRVKERVNDDFSDFSDFSLDLSRKFIDLSDKWKMPSESEIKEILSKIGKFSPE
DELNCGACGYDTCREKAIAVFNGMAEPYMCLPYMRGRAETLSNIIISSTPNAIIAVNNEYEIQDMNRAFEKM
FLVNSSMVKGEDLSLIFDISDFVEVIENKKSIFNKKVSFKNYGIIALESIYYLEEYKIAIGIFTDITKMEKQKESFSKL
KKENYQLAQQVIDRQMKVAQEIASLLGETTAETKVILTKMKDMLLNQGDDE (SEQ ID No. 6)

SEQUENCE LISTING

<160> NUMBER OF SEQ ID NOS: 8

<210> SEQ ID NO 1
<211> LENGTH: 81
<212> TYPE: PRT
<213> ORGANISM: Thermoanaerobacterium saccharolyticum

<400> SEQUENCE: 1

```
Met Val Ile Thr Val Cys Val Gly Ser Ser Cys His Leu Lys Gly Ser
1               5                   10                  15

Tyr Asp Val Ile Asn Lys Leu Lys Glu Met Ile Lys Asn Tyr Gly Ile
            20                  25                  30

Glu Asp Lys Val Glu Leu Lys Ala Asp Phe Cys Met Gly Asn Cys Leu
        35                  40                  45

Arg Ala Val Ser Val Lys Ile Asp Gly Gly Ala Cys Leu Ser Ile Lys
    50                  55                  60

Pro Asn Ser Val Glu Arg Phe Phe Lys Glu His Val Leu Gly Glu Leu
65                  70                  75                  80

Lys
```

<210> SEQ ID NO 2
<211> LENGTH: 81
<212> TYPE: PRT
<213> ORGANISM: Thermoanaerobacterium thermosaccharolyticum

```
<400> SEQUENCE: 2

Met Val Ile Thr Val Cys Val Gly Ser Ser Cys His Leu Lys Gly Ser
1               5                   10                  15

Tyr Asp Val Ile Asn Glu Leu Lys Lys Phe Ile Lys Asp Tyr Asn Leu
                20                  25                  30

Glu Asp Arg Val Glu Leu Lys Ala Asp Phe Cys Met Gly Asn Cys Leu
            35                  40                  45

Arg Ala Val Ser Val Lys Ile Asp Asp Gly Lys Cys Leu Ser Ile Lys
50                  55                  60

Pro Asn Asn Val Glu Lys Phe Phe Arg Glu Tyr Val Leu Gly Asn Leu
65                  70                  75                  80

Gln

<210> SEQ ID NO 3
<211> LENGTH: 81
<212> TYPE: PRT
<213> ORGANISM: Thermoanaerobacterium xylanolyticum

<400> SEQUENCE: 3

Met Val Ile Thr Val Cys Val Gly Ser Ser Cys His Leu Lys Gly Ser
1               5                   10                  15

Tyr Asp Val Ile Asn Lys Leu Lys Glu Met Ile Lys Asn Tyr Gly Ile
                20                  25                  30

Glu Asp Lys Val Glu Leu Lys Ala Asp Phe Cys Met Gly Asn Cys Leu
            35                  40                  45

Arg Ala Val Ser Val Lys Ile Asp Asp Gly Lys Cys Leu Ser Val Lys
50                  55                  60

Pro Asn Asn Val Glu Lys Phe Phe Lys Glu Tyr Val Leu Gly Glu Leu
65                  70                  75                  80

Lys

<210> SEQ ID NO 4
<211> LENGTH: 572
<212> TYPE: PRT
<213> ORGANISM: Thermoanaerobacterium saccharolyticum

<400> SEQUENCE: 4

Met Ser Val Ile Asn Phe Lys Glu Ala Asn Cys Arg Asn Cys Tyr Lys
1               5                   10                  15

Cys Ile Arg Tyr Cys Pro Val Lys Ala Ile Lys Val Asn Asp Glu Gln
                20                  25                  30

Ala Glu Ile Ile Glu Tyr Arg Cys Ile Ala Cys Gly Arg Cys Leu Asn
            35                  40                  45

Ile Cys Pro Gln Asn Ala Lys Thr Val Arg Ser Asp Val Glu Arg Val
50                  55                  60

Gln Ser Phe Leu Asn Lys Gly Glu Lys Val Ala Phe Thr Val Ala Pro
65                  70                  75                  80

Ser Tyr Pro Ala Leu Val Gly His Asp Gly Ala Leu Asn Phe Leu Lys
                85                  90                  95

Ala Leu Lys Ser Leu Gly Ala Glu Met Ile Val Glu Thr Ser Val Gly
            100                 105                 110

Ala Met Leu Ile Ser Lys Glu Tyr Glu Arg Tyr Tyr Asn Asp Leu Lys
        115                 120                 125
```

-continued

```
Tyr Asp Asn Leu Ile Thr Thr Ser Cys Pro Ser Val Asn Tyr Leu Val
    130                 135                 140

Glu Lys Tyr Tyr Pro Asp Leu Ile Lys Cys Leu Val Pro Val Val Ser
145                 150                 155                 160

Pro Met Val Ala Val Gly Arg Ala Ile Lys Asn Ile His Gly Glu Gly
                165                 170                 175

Val Lys Val Val Phe Ile Gly Pro Cys Leu Ala Lys Lys Ala Glu Met
            180                 185                 190

Ser Asp Phe Ser Cys Glu Gly Ala Ile Asp Ala Val Leu Thr Phe Glu
        195                 200                 205

Glu Val Met Asn Leu Phe Asn Thr Asn Lys Ile Gly Val Glu Cys Thr
    210                 215                 220

Lys Glu Asn Leu Glu Asp Val Asp Ser Glu Ser Arg Phe Lys Leu Tyr
225                 230                 235                 240

Pro Ile Glu Gly Lys Thr Met Asp Cys Met Asp Val Asp Leu Asn Leu
                245                 250                 255

Arg Lys Phe Ile Ser Val Ser Ser Ile Glu Asn Val Lys Asp Ile Leu
            260                 265                 270

Asn Asp Leu Arg Ala Gly Asn Leu His Gly Tyr Trp Ile Glu Ala Asn
        275                 280                 285

Ala Cys Asp Gly Gly Cys Ile Asn Gly Pro Ala Phe Gly Lys Leu Glu
    290                 295                 300

Ser Gly Ile Ala Lys Arg Lys Glu Glu Val Ile Ser Tyr Ser Arg Met
305                 310                 315                 320

Lys Glu Arg Phe Ser Gly Asp Phe Ser Gly Ile Thr Asp Phe Ser Leu
                325                 330                 335

Asp Leu Ser Arg Lys Phe Ile Asp Leu Ser Asp Arg Trp Lys Met Pro
            340                 345                 350

Ser Glu Met Glu Ile Lys Glu Ile Leu Ser Lys Ile Gly Lys Phe Ser
        355                 360                 365

Val Glu Asp Glu Leu Asn Cys Gly Ala Cys Gly Tyr Asp Thr Cys Arg
    370                 375                 380

Glu Lys Ala Ile Ala Val Phe Asn Gly Met Ala Glu Pro Tyr Met Cys
385                 390                 395                 400

Leu Pro Tyr Met Arg Gly Arg Ala Glu Thr Leu Ser Asn Ile Ile
                405                 410                 415

Ser Ser Thr Pro Asn Ala Ile Ile Ala Val Asn Asn Glu Tyr Glu Ile
            420                 425                 430

Gln Asp Met Asn Arg Ala Phe Glu Lys Met Phe Leu Val Asn Ser Ala
        435                 440                 445

Met Val Lys Gly Glu Asp Leu Ser Leu Ile Phe Asp Ile Ser Asp Phe
    450                 455                 460

Val Glu Val Ile Glu Asn Lys Lys Ser Ile Phe Asn Lys Lys Val Ser
465                 470                 475                 480

Phe Lys Asn Tyr Gly Ile Ile Ala Leu Glu Ser Ile Tyr Tyr Leu Glu
                485                 490                 495

Glu Tyr Lys Ile Ala Ile Gly Ile Phe Thr Asp Ile Thr Lys Met Glu
            500                 505                 510

Lys Gln Lys Glu Ser Phe Ser Lys Leu Lys Arg Glu Asn Tyr Gln Leu
        515                 520                 525

Ala Gln Gln Val Ile Asp Arg Gln Met Lys Val Ala Gln Glu Ile Ala
    530                 535                 540
```

```
Ser Leu Leu Gly Glu Thr Thr Ala Glu Thr Lys Val Ile Leu Thr Lys
545                 550                 555                 560

Met Lys Asp Met Leu Leu Asn Gln Gly Asp Asp Glu
            565                 570
```

<210> SEQ ID NO 5
<211> LENGTH: 572
<212> TYPE: PRT
<213> ORGANISM: Thermoanaerobacterium thermosaccharolyticum

<400> SEQUENCE: 5

```
Met Ser Val Ile Asn Phe Lys Glu Ala Asn Cys Arg Asn Cys Tyr Lys
1               5                   10                  15

Cys Ile Arg Tyr Cys Pro Val Lys Ala Ile Lys Val Asn Asn Glu Gln
            20                  25                  30

Ala Glu Ile Val Asp Tyr Met Cys Ile Ala Cys Gly Arg Cys Leu Asn
        35                  40                  45

Val Cys Pro Gln Asn Ala Lys Thr Val Arg Ser Asp Ile Glu Lys Val
50                  55                  60

Lys Ala Phe Ile Lys Lys Gly Asp Lys Val Val Phe Thr Ile Ala Pro
65                  70                  75                  80

Ser Tyr Pro Ala Leu Val Gly Ser Gly Arg Ala Phe Lys Phe Leu Asn
                85                  90                  95

Ala Leu Lys Ser Leu Gly Ala Glu Met Ile Glu Thr Ser Val Gly
            100                 105                 110

Ala Met Phe Ile Ser Lys Glu Tyr Glu Arg Tyr Tyr Asn Asp Leu Lys
        115                 120                 125

Tyr Asp Asn Leu Ile Thr Thr Ser Cys Pro Ser Ile Asn Tyr Leu Ile
130                 135                 140

Glu Lys Tyr Tyr Pro Asp Leu Ile Asn Cys Leu Val Pro Val Val Ser
145                 150                 155                 160

Pro Met Ile Ala Val Gly Arg Val Val Lys Lys Val Tyr Gly Asn Glu
                165                 170                 175

Ile Lys Val Val Phe Ile Gly Pro Cys Leu Ala Lys Lys Val Glu Met
            180                 185                 190

Asn Asp Phe Ser Cys Glu Asp Ala Ile Asp Ala Val Leu Thr Phe Glu
        195                 200                 205

Glu Ile Ile Glu Trp Leu Asp Gly Asp Gly Ile Asn Ile Asp Ser Arg
210                 215                 220

Glu Glu Phe Thr Asp Cys Val Asp Thr Met Met Pro Phe Lys Leu Tyr
225                 230                 235                 240

Pro Ile Glu Gly Lys Thr Ile Asp Cys Met Asp Val Asp Leu Asn Leu
                245                 250                 255

Arg Lys Val Val Ser Val Ser Ser Ile Asp Asn Val Lys Asp Leu Leu
            260                 265                 270

Asn Asp Ile Arg Ser Gly Asn Leu His Gly Tyr Trp Ile Glu Ala Asn
        275                 280                 285

Ala Cys Asp Gly Gly Cys Ile Asn Gly Pro Ala Phe Gly Arg Ser Asn
290                 295                 300

Ser Gly Val Val Lys Arg Lys Glu Glu Val Ile Asn Tyr Ser Asn Thr
305                 310                 315                 320

Lys Ala Asn Phe Ile Asn Asp Ile Ser Asn Met Ile Asp Cys Ser Val
                325                 330                 335

Asp Phe Thr Arg Lys Phe Ile Asn Leu Ser Asp Lys Trp Lys Met Pro
            340                 345                 350
```

```
Ser Glu Asn Glu Ile Lys Asn Ile Leu Ser Lys Ile Gly Lys Phe Thr
            355                 360                 365

Lys Glu Asp Glu Leu Asn Cys Gly Ala Cys Gly Tyr Asp Thr Cys Arg
    370                 375                 380

Glu Lys Ala Ile Ala Val Phe Asn Gly Met Ala Glu Pro Tyr Met Cys
385                 390                 395                 400

Leu Pro Tyr Met Arg Gly Arg Ala Glu Thr Leu Ser Asn Ile Ile Ile
            405                 410                 415

Ser Ser Thr Pro Asn Ala Ile Ile Ala Val Asn Asn Glu Tyr Glu Ile
            420                 425                 430

Gln Asp Met Asn Arg Ala Phe Glu Lys Met Phe Leu Val Asn Ser Thr
            435                 440                 445

Met Val Lys Asn Glu Asn Leu Ser Leu Ile Phe Asp Ile Ser Asp Phe
            450                 455                 460

Lys Asp Val Ile Glu Asn Lys Lys Ser Ile Phe Asn Lys Lys Val Ser
465                 470                 475                 480

Phe Lys Asn Tyr Gly Ile Ile Ala Leu Glu Ser Ile Tyr Tyr Leu Glu
            485                 490                 495

Glu Tyr Lys Ile Ala Ile Gly Ile Phe Thr Asp Ile Thr Lys Met Glu
            500                 505                 510

Lys Gln Lys Glu Ala Phe Ser Lys Val Lys Arg Glu Asn Tyr Gln Leu
            515                 520                 525

Ala Gln Gln Val Ile Asp Arg Gln Met Lys Val Ala Gln Glu Ile Ala
            530                 535                 540

Ser Leu Leu Gly Glu Thr Thr Ala Glu Thr Lys Val Ile Leu Thr Arg
545                 550                 555                 560

Met Lys Asp Met Leu Leu Asn Gln Gly Asp Asp Glu
            565                 570

<210> SEQ ID NO 6
<211> LENGTH: 572
<212> TYPE: PRT
<213> ORGANISM: Thermoanaerobacterium xylanolyticum

<400> SEQUENCE: 6

Met Ser Val Ile Asn Phe Lys Glu Ala Asn Cys Arg Asn Cys Tyr Lys
1               5                   10                  15

Cys Ile Arg Tyr Cys Pro Val Lys Ala Ile Lys Val Asn Asn Glu Gln
            20                  25                  30

Ala Glu Ile Ile Glu Tyr Arg Cys Ile Ala Cys Gly Arg Cys Leu Asn
            35                  40                  45

Ile Cys Pro Gln Asn Ala Lys Thr Val Arg Ser Asp Val Glu Ile Val
    50                  55                  60

Gln Ser Phe Leu Asn Arg Gly Glu Lys Val Val Phe Thr Val Ala Pro
65                  70                  75                  80

Ser Tyr Pro Ala Leu Val Gly His Asn Asn Ala Leu Lys Phe Leu Lys
            85                  90                  95

Ala Leu Lys Ser Leu Gly Ala Glu Met Ile Val Glu Thr Ser Val Gly
            100                 105                 110

Ala Met Leu Ile Ser Lys Glu Tyr Glu Lys Tyr Asn Asp Leu Lys
            115                 120                 125

Tyr Asp Asn Leu Ile Thr Thr Ser Cys Pro Ser Val Asn Tyr Leu Val
            130                 135                 140

Glu Lys Tyr Tyr Pro Asp Leu Ile Asn Cys Leu Val Pro Val Val Ser
145                 150                 155                 160
```

-continued

```
Pro Met Val Ala Val Gly Arg Ala Ile Lys Ile Met Tyr Gly Glu Ser
            165                 170                 175

Met Lys Val Val Phe Ile Gly Pro Cys Leu Ala Lys Lys Ala Glu Met
            180                 185                 190

Asn Asp Phe Ser Cys Glu Gly Ala Ile Asp Ala Val Leu Thr Phe Glu
            195                 200                 205

Glu Val Met Asn Leu Leu Gly Thr Asp Glu Val Asp Phe Glu Tyr Met
        210                 215                 220

Glu Asp Tyr Leu Glu Asp Val Asp Val Glu Gln Tyr Lys Leu Tyr
225                 230                 235                 240

Pro Ile Glu Gly Lys Thr Ile Asp Cys Met Asp Val Asp Leu Asn Leu
            245                 250                 255

Arg Lys Val Val Ser Val Ser Ser Ile Glu Asn Val Lys Asp Leu Leu
            260                 265                 270

Asn Asp Leu Arg Tyr Gly Asn Leu His Gly Tyr Trp Ile Glu Ala Asn
            275                 280                 285

Ala Cys Asp Gly Gly Cys Ile Asn Gly Pro Ala Phe Gly Lys Leu Lys
            290                 295                 300

Ser Gly Ile Ala Lys Arg Lys Glu Val Ile Ser Tyr Ser Arg Val
305                 310                 315                 320

Lys Glu Arg Val Asn Asp Asp Phe Ser Asp Phe Ser Asp Phe Ser Leu
            325                 330                 335

Asp Leu Ser Arg Lys Phe Ile Asp Leu Ser Asp Lys Trp Lys Met Pro
            340                 345                 350

Ser Glu Ser Glu Ile Lys Glu Ile Leu Ser Lys Ile Gly Lys Phe Ser
            355                 360                 365

Pro Glu Asp Glu Leu Asn Cys Gly Ala Cys Gly Tyr Asp Thr Cys Arg
            370                 375                 380

Glu Lys Ala Ile Ala Val Phe Asn Gly Met Ala Glu Pro Tyr Met Cys
385                 390                 395                 400

Leu Pro Tyr Met Arg Gly Arg Ala Glu Thr Leu Ser Asn Ile Ile Ile
            405                 410                 415

Ser Ser Thr Pro Asn Ala Ile Ile Ala Val Asn Asn Glu Tyr Glu Ile
            420                 425                 430

Gln Asp Met Asn Arg Ala Phe Glu Lys Met Phe Leu Val Asn Ser Ser
            435                 440                 445

Met Val Lys Gly Glu Asp Leu Ser Leu Ile Phe Asp Ile Ser Asp Phe
            450                 455                 460

Val Glu Val Ile Glu Asn Lys Lys Ser Ile Phe Asn Lys Lys Val Ser
465                 470                 475                 480

Phe Lys Asn Tyr Gly Ile Ile Ala Leu Glu Ser Ile Tyr Tyr Leu Glu
            485                 490                 495

Glu Tyr Lys Ile Ala Ile Gly Ile Phe Thr Asp Ile Thr Lys Met Glu
            500                 505                 510

Lys Gln Lys Glu Ser Phe Ser Lys Leu Lys Lys Glu Asn Tyr Gln Leu
            515                 520                 525

Ala Gln Gln Val Ile Asp Arg Gln Met Lys Val Ala Gln Glu Ile Ala
            530                 535                 540

Ser Leu Leu Gly Glu Thr Thr Ala Glu Thr Lys Val Ile Leu Thr Lys
545                 550                 555                 560

Met Lys Asp Met Leu Leu Asn Gln Gly Asp Asp Glu
            565                 570
```

```
<210> SEQ ID NO 7
<211> LENGTH: 386
<212> TYPE: PRT
<213> ORGANISM: Thermoanaerobacterium saccharolyticum

<400> SEQUENCE: 7
```

| | | | | | | | | | | | | | | | |
|---|---|---|---|---|---|---|---|---|---|---|---|---|---|---|---|
| Met | Ser | His | Tyr | Ile | Asp | Ile | Ala | His | Ala | Ser | Leu | Asn | Lys | Tyr | Asp |
| 1 | | | | 5 | | | | | 10 | | | | | 15 | |
| Glu | Glu | Leu | Cys | Gly | Asp | Ser | Val | Gln | Ile | Ile | Arg | Lys | Lys | Asp | Tyr |
| | | | 20 | | | | | 25 | | | | | 30 | | |
| Ala | Met | Ala | Val | Met | Ala | Asp | Gly | Leu | Gly | Ser | Gly | Val | Lys | Ala | Asn |
| | | 35 | | | | | 40 | | | | | 45 | | | |
| Ile | Leu | Ser | Thr | Leu | Thr | Thr | Arg | Ile | Val | Ser | Lys | Met | Leu | Asp | Met |
| | 50 | | | | | 55 | | | | | 60 | | | | |
| Gly | Ser | Glu | Leu | Arg | Asp | Val | Val | Glu | Thr | Val | Ala | Glu | Thr | Leu | Pro |
| 65 | | | | | 70 | | | | | 75 | | | | | 80 |
| Ile | Cys | Lys | Glu | Arg | Asn | Ile | Ala | Tyr | Ser | Thr | Phe | Thr | Val | Val | Ser |
| | | | | 85 | | | | | 90 | | | | | 95 | |
| Ile | Tyr | Gly | Asp | Asn | Ala | His | Leu | Val | Glu | Tyr | Asp | Asn | Pro | Ser | Val |
| | | | 100 | | | | | 105 | | | | | 110 | | |
| Phe | Tyr | Phe | Lys | Asn | Gly | Val | His | Lys | Lys | Val | Asp | Arg | Lys | Cys | Val |
| | | 115 | | | | | 120 | | | | | 125 | | | |
| Glu | Ile | Gly | Asp | Lys | Lys | Ile | Phe | Glu | Ser | Ser | Phe | Lys | Leu | Asp | Leu |
| | 130 | | | | | 135 | | | | | 140 | | | | |
| Asn | Asp | Ala | Leu | Ile | Val | Val | Ser | Asp | Gly | Val | Ile | His | Ala | Gly | Val |
| 145 | | | | | 150 | | | | | 155 | | | | | 160 |
| Gly | Gly | Ile | Leu | Asn | Leu | Gly | Trp | Gln | Trp | Asp | Asn | Val | Lys | Gln | Tyr |
| | | | | 165 | | | | | 170 | | | | | 175 | |
| Leu | Ser | Lys | Val | Leu | Glu | Val | Tyr | Ser | Asp | Ala | Ser | Asp | Ile | Cys | Ser |
| | | | 180 | | | | | 185 | | | | | 190 | | |
| Gln | Leu | Ile | Thr | Thr | Cys | Asn | Asn | Leu | Tyr | Lys | Asn | Arg | Pro | Gly | Asp |
| | | 195 | | | | | 200 | | | | | 205 | | | |
| Asp | Thr | Thr | Ala | Ile | Val | Ile | Lys | Val | Asn | Glu | Ser | Lys | Lys | Val | Thr |
| | 210 | | | | | 215 | | | | | 220 | | | | |
| Val | Met | Val | Gly | Pro | Pro | Ile | Leu | Lys | Asn | Met | Asp | Glu | Trp | Val | Val |
| 225 | | | | | 230 | | | | | 235 | | | | | 240 |
| Lys | Lys | Leu | Met | Lys | Ser | Glu | Gly | Leu | Lys | Val | Val | Cys | Gly | Gly | Thr |
| | | | | 245 | | | | | 250 | | | | | 255 | |
| Ala | Ala | Lys | Ile | Val | Ser | Arg | Ile | Leu | Asn | Lys | Asp | Val | Ile | Thr | Ser |
| | | | 260 | | | | | 265 | | | | | 270 | | |
| Thr | Glu | Tyr | Ile | Asp | Pro | Asp | Ile | Pro | Pro | Tyr | Ala | His | Ile | Asp | Gly |
| | | 275 | | | | | 280 | | | | | 285 | | | |
| Ile | Asp | Leu | Val | Thr | Glu | Gly | Val | Leu | Thr | Leu | Arg | Lys | Thr | Val | Glu |
| | 290 | | | | | 295 | | | | | 300 | | | | |
| Ile | Phe | Lys | Glu | Tyr | Met | Asn | Asp | Lys | Asp | Ser | Asn | Leu | Leu | Arg | Phe |
| 305 | | | | | 310 | | | | | 315 | | | | | 320 |
| Ser | Lys | Lys | Asp | Ala | Ala | Thr | Arg | Leu | Phe | Lys | Ile | Leu | Asn | Tyr | Ala |
| | | | | 325 | | | | | 330 | | | | | 335 | |
| Thr | Asp | Val | Asn | Phe | Leu | Val | Gly | Gln | Ala | Val | Asn | Ser | Ala | His | Gln |
| | | | 340 | | | | | 345 | | | | | 350 | | |
| Asn | Pro | Asp | Phe | Pro | Ser | Asp | Leu | Arg | Ile | Lys | Val | Arg | Ile | Val | Glu |
| | | 355 | | | | | 360 | | | | | 365 | | | |

Glu Leu Ile Ser Leu Leu Glu Arg Leu Asn Lys Asn Val Glu Val Asn
    370                 375                 380

Tyr Phe
385

<210> SEQ ID NO 8
<211> LENGTH: 504
<212> TYPE: PRT
<213> ORGANISM: Thermoanaerobacterium saccharolyticum

<400> SEQUENCE: 8

Leu Phe Lys Phe Asn Thr Asp Val Gln Met Leu Lys Tyr Glu Val Leu
1               5                   10                  15

Tyr Asn Val Ala Lys Leu Thr Leu Glu Asp Arg Leu Glu Asp Glu Tyr
            20                  25                  30

Asp Glu Ile Pro Tyr Glu Ile Ile Pro Gly Thr Lys Pro Arg Phe Arg
        35                  40                  45

Cys Cys Val Tyr Lys Glu Arg Ala Ile Ile Glu Gln Arg Thr Lys Val
    50                  55                  60

Ala Met Gly Lys Asn Leu Lys Arg Thr Met Lys His Ala Val Asp Gly
65              70                  75                  80

Glu Glu Pro Ile Ile Gln Val Leu Asp Ile Ala Cys Glu Glu Cys Pro
                85                  90                  95

Ile Lys Arg Tyr Arg Val Thr Glu Ala Cys Arg Gly Cys Ile Thr His
            100                 105                 110

Arg Cys Thr Glu Val Cys Pro Lys Gly Ala Ile Thr Ile Ile Asn Lys
        115                 120                 125

Lys Ala Asn Ile Asp Tyr Asp Lys Cys Ile Glu Cys Gly Arg Cys Lys
    130                 135                 140

Asp Ala Cys Pro Tyr Asn Ala Ile Ser Asp Asn Leu Arg Pro Cys Ile
145                 150                 155                 160

Arg Ser Cys Ser Ala Lys Ala Ile Thr Met Asp Glu Glu Leu Lys Ala
                165                 170                 175

Ala Ile Asn Tyr Glu Lys Cys Thr Ser Cys Gly Ala Cys Thr Leu Ala
            180                 185                 190

Cys Pro Phe Gly Ala Ile Thr Asp Lys Ser Tyr Ile Val Asp Ile Ile
        195                 200                 205

Arg Ala Ile Lys Ser Gly Lys Lys Val Tyr Ala Leu Val Ala Pro Ala
    210                 215                 220

Ile Ala Ser Gln Phe Lys Asp Val Thr Val Gly Gln Ile Lys Ser Ala
225                 230                 235                 240

Leu Lys Glu Phe Gly Phe Val Asp Val Ile Glu Val Ala Leu Gly Ala
                245                 250                 255

Asp Phe Val Ala Met Glu Glu Ala Lys Glu Phe Ser His Lys Ile Lys
            260                 265                 270

Asp Ile Lys Val Met Thr Ser Ser Cys Cys Pro Ala Phe Val Ala His
        275                 280                 285

Ile Lys Lys Ser Tyr Pro Glu Leu Ser Gln Asn Ile Ser Thr Thr Val
    290                 295                 300

Ser Pro Met Thr Ala Ile Ser Lys Tyr Ile Lys Lys His Asp Pro Met
305                 310                 315                 320

Ala Val Thr Val Phe Ile Gly Pro Cys Thr Ala Lys Lys Ser Glu Val
                325                 330                 335

Met Arg Asp Asp Val Lys Gly Ile Thr Asp Phe Ala Met Thr Phe Glu
            340                 345                 350

-continued

```
Glu Met Val Ala Val Leu Asp Ala Ala Lys Ile Asp Met Lys Glu Gln
    355                 360                 365
Gln Asp Val Glu Val Asp Asp Ala Thr Leu Phe Gly Arg Lys Phe Ala
    370                 375                 380
Arg Ser Gly Gly Val Leu Glu Ala Val Val Glu Ala Val Lys Glu Ile
385                 390                 395                 400
Gly Ala Asp Val Glu Val Asn Pro Val Val Cys Asn Gly Leu Asp Glu
                405                 410                 415
Cys Asn Lys Thr Leu Lys Ile Met Lys Ala Gly Lys Leu Pro Asn Asn
            420                 425                 430
Phe Ile Glu Gly Met Ala Cys Ile Gly Gly Cys Ile Gly Gly Ala Gly
        435                 440                 445
Val Ile Asn Asn Asn Val Asn Gln Ala Lys Leu Ala Val Asn Lys Phe
    450                 455                 460
Gly Asp Ser Ser Tyr His Lys Ser Ile Lys Asp Arg Ile Ser Gln Phe
465                 470                 475                 480
Asp Thr Asp Asp Val Asp Phe His Val Asp Ser Gly Glu Asp Glu Ser
                485                 490                 495
Ser Glu Thr Ser Phe Lys Glu Ala
            500
```

INCREASED ETHANOL PRODUCTION BY THERMOPHILIC MICROORGANISMS WITH DELETION OF INDIVIDUAL HFS HYDROGENASE SUBUNITS

RELATED APPLICATION

This application claims priority to U.S. Patent application 62/365,200 filed Jul. 21, 2016, the entire content of which is hereby incorporated by reference into this application.

GOVERNMENT INTERESTS

This invention was made with government support under Award No. DE-AC05-00OR-22725 awarded by the BioEnergy Science Center (BESC) under the Department of Energy. The government has certain rights in this invention.

REFERENCE TO SEQUENCE LISTING

A sequence listing containing SEQ ID NOs. 1-8 is submitted herewith and is specifically incorporated by reference.

BACKGROUND

I. Field of the Invention

The disclosure relates to conversion of biomass to biofuel or other useful products. More particularly, the disclosure pertains to the generation of microorganisms having higher ethanol yields.

II. Description of the Related Art

Thermophilic bacteria have been engineered to produce ethanol from the cellulose and/or hemicellulose fractions of biomass. Examples of such thermophilic bacteria include *Clostridium thermocellum* and *Thermoanaerobacterium saccharolyticum*, among others.

*Thermoanaerobacterium saccharolyticum* is a thermophilic, anaerobic bacterium able to ferment hemicellulose but not cellulose. Wild-type strains produce ethanol, acetic acid and under certain conditions, lactic acid as the main fermentation products.

*Thermoanaerobacterium saccharolyticum* may consume a variety of sugars derived from the hemicellulose fraction of lignocellulosic biomass and convert them to acetate, lactate and ethanol. A number of strategies have been pursued to engineer this organism for increased ethanol production. Generally these strategies involve deleting genes for lactate production, acetate production or both. These strategies have helped improve the ethanol yield, but each approach has its own limitations.

The primary hydrogenase in *T. saccharolyticum* is called hfs, which has four subunits, hfsA, hfsB, hfsC and hfsD. Complete deletion of all four subunits (A, B, C and D) has been reported (Shaw et al. 2009). Deletion of hfs (A, B, C and D subunits) does not increase ethanol yield. Deletion of hfs and ldh in combination increases ethanol yield by 44%. In a different approach, a mutant hfs operon (called hfs*), containing several point mutations from a high-ethanol-producing strain, is re-introduced into the wild-type strain. The resultant strain shows 36% increase in ethanol yield as compared to the parental strain (Shaw et al. 2015).

SUMMARY

The presently disclosed instrumentalities advance the art by providing methods for engineering a thermophilic bacterium to produce ethanol at high yield by deleting a single gene. In one embodiment, it is shown here that single deletion of hfsA or hfsB allows for increased ethanol yield in a variety of thermophilic bacterial strains. In another embodiment, although deleting hydrogenases is typically accompanied by an increase in lactate production, deletion of the hfsA or hfsB, as shown here, does not result in a substantial increase in lactate production.

In one embodiment, the present disclosure provides *T. saccharolyticum* strains in which subunit A and/or subunit B (but not subunit C or subunit D) is disrupted. The resultant strain shows an increase of ethanol yield by 77% as compared to the parental strain (FIGS. 2A and 2B). In another embodiment, microorganisms suitable for the improvement from hfs deletions may include but are not limited to the genus of *Thermoanaerobacterium*. Examples of such microorganisms may include, *Thermoanaerobacterium saccharolyticum, Thermoanaerobacterium thermosaccharolyticum* and *Thermoanaerobacterium xylanolyticum*. The same or similar hfs deletions may be applied to these other organisms as well.

In one embodiment, a genetically engineered microorganism is disclosed, which comprises a functional hfsC subunit and/or a functional hfsD subunit of the hfs hydrogenase, wherein expression of at least one subunit of the hfs hydrogenase is disrupted. The disrupted subunit may be hfsA and/or hfsB, and there may be only one or two disrupted subunits. For purpose of this disclosure, the term "functional" means the protein is performing the same or substantially the same role as its counterpart in a wild-type strain. In one aspect, the disclosed microorganism may belong to the genus of *Thermoanaerobacterium*. In another aspect, the disclosed microorganism may be selected from the group consisting of *Thermoanaerobacterium saccharolyticum, Thermoanaerobacterium thermosaccharolyticum* and *Thermoanaerobacterium xylanolyticum*.

In another embodiment, the disclosed microorganism may have an ethanol yield that is equal to or greater than 70%, 80% or 90% of theoretical yield.

In another embodiment, the disclosed microorganism may have intact or functional pta and ack genes. In one aspect, the sequences of the pta and ack genes in the disclosed microorganism are identical to the pta and ack genes in a wildtype strain of the same species.

In another embodiment, the disclosed microorganism may have intact or functional ldh gene. In one aspect, the sequence of the ldh gene is identical to the ldh gene in a wildtype strain of the same species.

In another embodiment, the HfsA protein of the disclosed microorganism of may be at least 45, 60, 70, 80, 90, 95% or 100% identical to a sequence selected from the group consisting of SEQ ID No. 1, SEQ ID No. 2 and SEQ ID No. 3.

In another embodiment, the HfsB protein of the disclosed microorganism of may be at least 45, 60, 70, 80, 90, 95% or 100% identical to a sequence selected from the group consisting of SEQ ID No. 4, SEQ ID No. 5 and SEQ ID No. 6.

Figure 3:
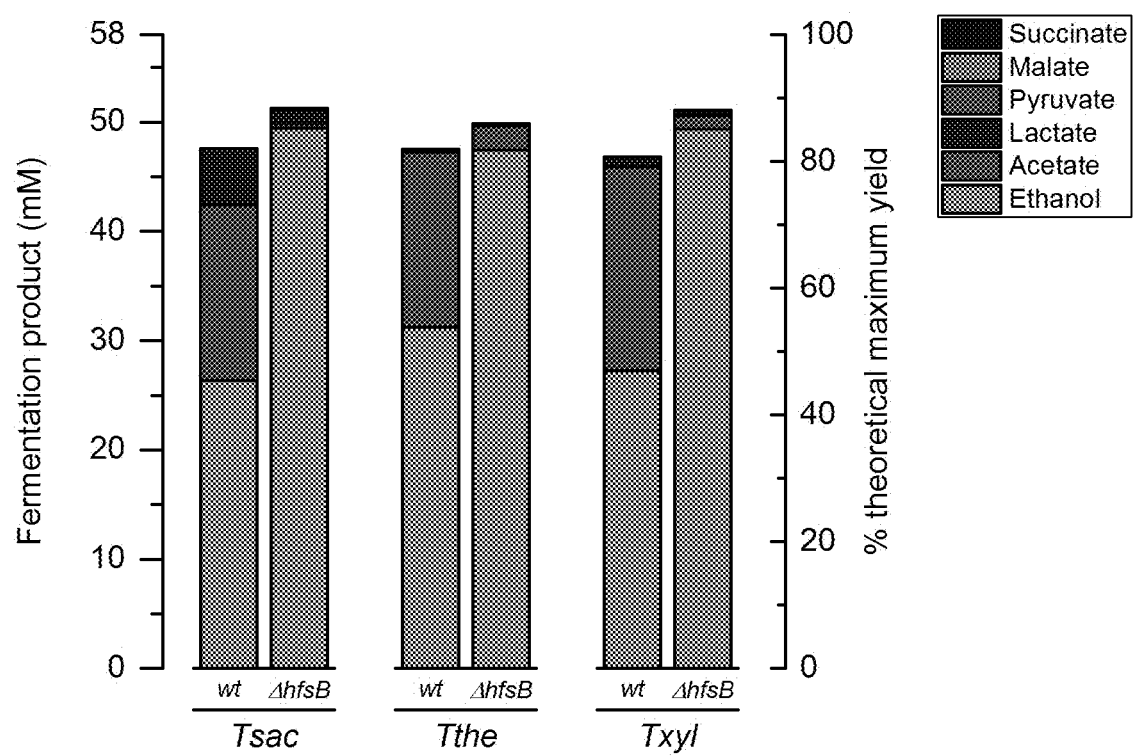

FIG. 3 shows fermentation data for a *Thermoanaerobacterium thermosaccharolyticum* strain and a *Thermoanaerobacterium xylanolyticum* strain with hfsB deletions as compared with wild-type strains. Strains were grown on 5 g/l cellobiose.

Figure 4:
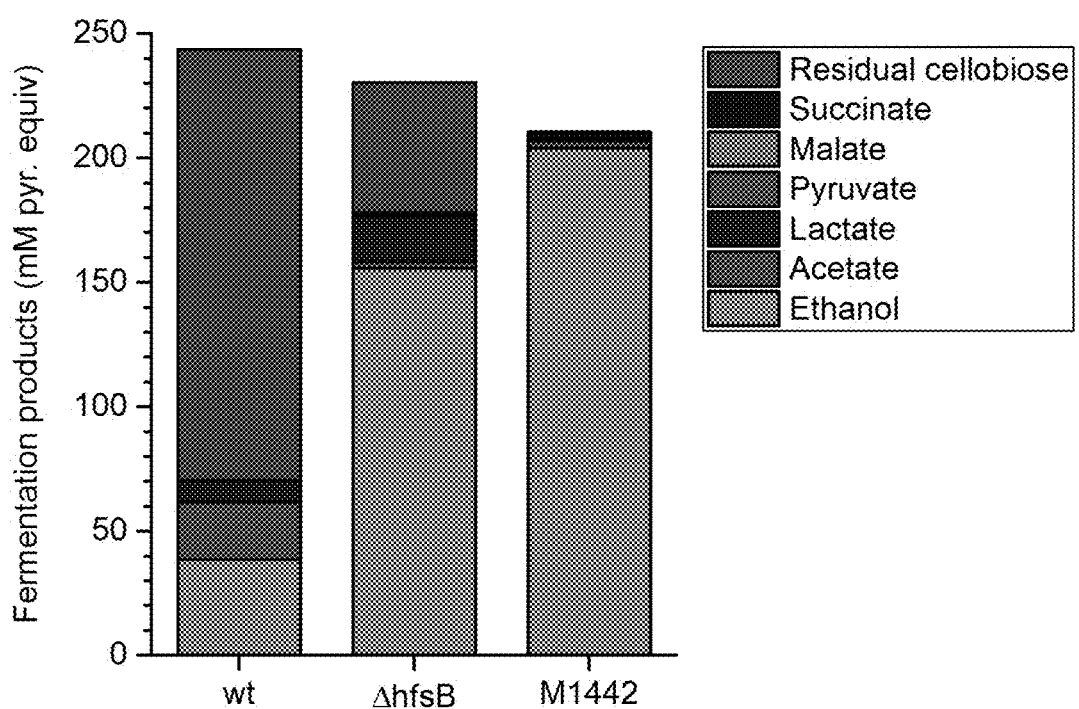

FIG. 4 shows fermentation data for *T. saccharolyticum* strains grown on 20 g/l cellobiose. Data are presented in units of "mM pyruvate equivalents." For succinate, malate, pyruvate, lactate, acetate and ethanol, one mM is equivalent to one mM of pyruvate. For cellobiose, one mM is equivalent to four mM of pyruvate. Strain M1442 (aka LL1049) is a strain of *T. saccharolyticum* engineered for high ethanol production with several deletions, as follows Δ(pta-ack) Δldh Δor795::metE-ure Δeps.

FIGS. 5A-5B show the sequences of the hfsA, B, C and D in *Thermoanaerobacterium saccharolyticum* and the sequences of hfsA and hfsB subunits in *Thermoanaerobacterium thermosaccharolyticum* and *Thermoanaerobacterium xylanolyticum*.

Figure 6:
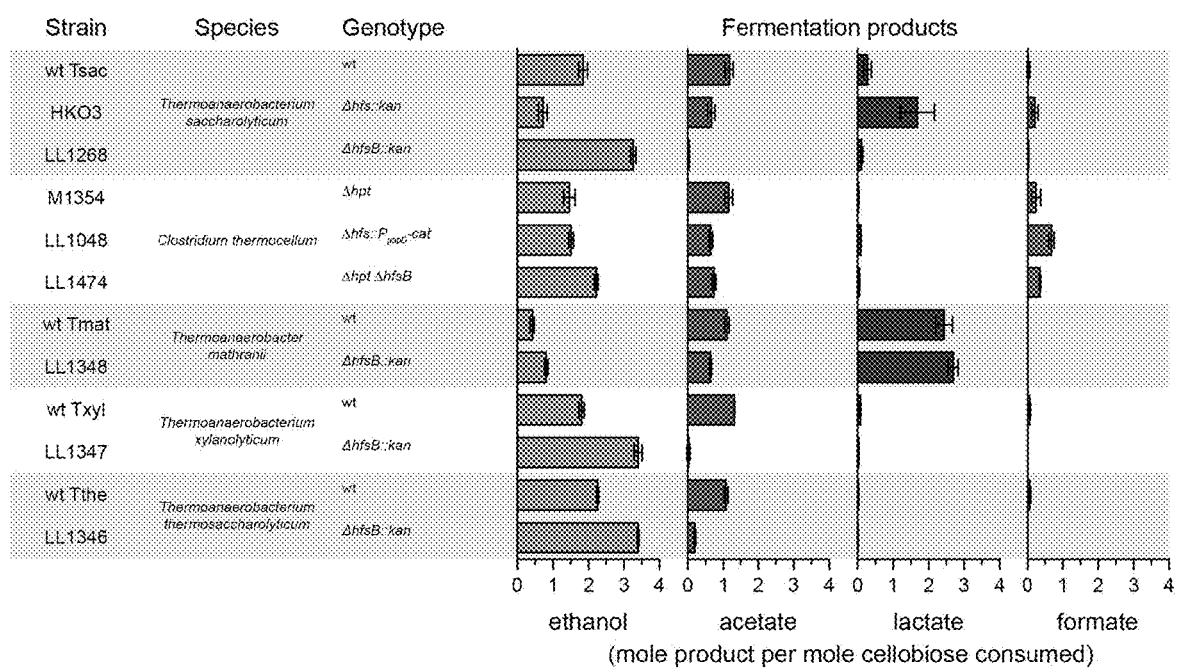

FIG. 6 shows fermentation products from various organisms with deletions of their hfs genes. Strains were grown on 5 g/l (14.7 mM) cellobiose. Error bars represent one standard deviation, n≥3.

DETAILED DESCRIPTION

Disclosed here are methods to generate microorganisms capable of producing ethanol from lignocellulosic feedstock with high yield. In one embodiment, disruption of specific subunits of the hfs hydrogenase are shown to result in higher ethanol yield in *Thermoanaerobacterium saccharolyticum*.

Figure 1:
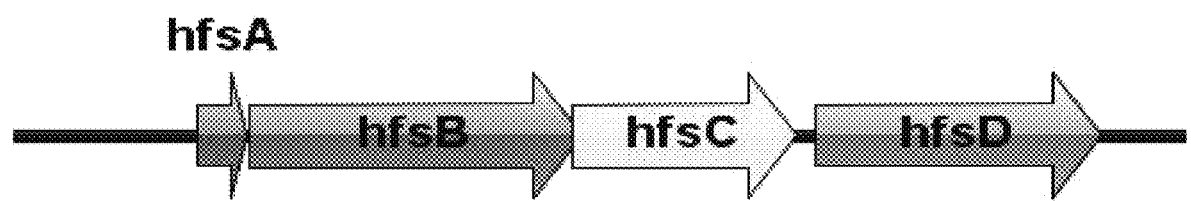
FIG. 1 shows the operon of the hfs gene showing the relative position and size of subunits A, B, C and D.

The primary hydrogenase in *T. saccharolyticum* is called hfs, which consists of 4 subunits, hfsA, hfsB, hfsC and hfsD (FIG. 1). Sequences of these genes and the encoded proteins in *T. saccharolyticum* and other species have been described in, for example, Shaw A J, et al., Metabolic engineering of a thermophilic bacterium to produce ethanol at high yield. Proc. Natl. Acad. Sci. U.S.A. 2008, 105:13769-74; Herring C D, et al., Strain and bioprocess improvement of a thermophilic anaerobe for the production of ethanol from wood. Biotechnol. Biofuels 2016, 9:125; Shaw A J, et al., Identification of the [FeFe]-hydrogenase responsible for hydrogen generation in *Thermoanaerobacterium saccharolyticum* and demonstration of increased ethanol yield via hydrogenase knockout. J. Bacteriol. 2009, 191:6457-64. It has been shown that the hfs hydrogenase is responsible for $H_2$ production in *T. saccharolyticum*. Deletion of the hfs operon has been shown to result in a decrease in $H_2$ and acetate, but no change in ethanol production. In a previous report, all 4 subunits of the hfs gene have been deleted in one strain. However, no significant increase in ethanol yield has been observed in the strain in which all 4 subunits have been deleted.

In one embodiment, it is disclosed that when the hfsA and/or hfsB gene is deleted in *Thermoanaerobacterium* organisms, such as *Thermoanaerobacterium saccharolyticum*, *Thermoanaerobacterium thermosaccharolyticum*, and *Thermoanaerobacterium xylanolyticum*, the resultant strains have increased ethanol yield. Even on 20 g/l cellobiose, the strains may perform almost as well as another engineered strains, M1442 (Δ(pta-ack) Δldh Δor795::metE-ure Δeps).

This genetic modification is a quick way to generate high-ethanol-producing strains. In another embodiment, these hfsA or hfsB deletion strains may be paired with cellulolytic strains (i.e. *C. thermocellum*) to convert plant biomass into ethanol.

Various manipulations of bacteria, DNA/RNA and protein may be performed as described in the literature. Transgenic and homologous recombination in *Thermoanaerobacterium saccharolyticum* may be performed as described in Shaw, A. J., Covalla, S. F., Hogsett, D. A & Herring, C. D. Marker removal system for *Thermoanaerobacterium saccharolyticum* and development of a markerless ethanologen. Appl. Environ. Microbiol. 77, 2534-6 (2011) and Shaw, A. J., Hogsett, D. A. & Lynd, L. R. Natural competence in *Thermoanaerobacter* and *Thermoanaerobacterium* species. Appl. Environ. Microbiol. 76, 4713-4719 (2010).

The term "biomass" refers to non-fossilized renewable materials that are derived from or produced by living organisms. In its broadest term, biomass may include animal biomass, plant biomass, and human waste and recycled materials, among others. Examples of animal biomass may include animal by-product and animal waste, etc. In one embodiment of this disclosure, biomass refers to plant biomass which includes any plant-derived matter (woody or non-woody) that is available on a sustainable basis. Plant biomass may include, but is not limited to, agricultural crop wastes and residues such as corn stover, corn processing byproducts such as corn bran or corn fiber, wheat straw, rice straw, sugar cane bagasse and the like, grass crops, such as switch grass, alfalfa, winter rye, and the like. Plant biomass may further include, but is not limited to, woody energy crops, wood wastes and residues such as trees, softwood forest thinnings, barky wastes, sawdust, paper and pulp industry residues or waste streams, wood fiber, and the like. In urban areas, plant biomass may include yard waste, such as grass clippings, leaves, tree clippings, brush, etc., vegetable processing waste, as well as recycled cardboard and paper products.

In one embodiment, grassy biomass may be used in the present disclosure. In another embodiment, winter cover crops such as winter rye may be used as a bioenergy feedstock using existing equipment and knowhow. Winter cover crops have little and arguably no competition with food crops for land or revenue, and they also positively impact soil and water quality as well as farm income, and offer important co-product opportunities. A recent study estimated that 200 million dry tons of winter rye per year could be produced in the U.S. on land used to grow corn and soybeans, which has a liquid fuel production potential equal to that of the current U.S. and Brazilian industries combined.

By using the system and methods disclosed herein, other cellulosic feedstocks may also be processed into biofuels without pretreatment. Examples of microorganisms may include but are not limited to *Thermoanaerobacterium saccharolyticum*, *Thermoanaerobacterium thermosaccharolyticum*, *Thermoanaerobacterium xylanolyticum*, *Clostridium thermocellum*, *Clostridium clariflavum*, *Caldicellulosiruptor bescii*, or *Clostridium thermocellum/Thermoanaerobacterium saccharolyticum* co-culture as fermentation systems. Various techniques known in the art for enhancing ethanol yield may be employed to further enhance the conversion.

The terms "disrupted" or "disruption of a gene" means the functionality of a gene is manipulated such that the disrupted gene no longer leads to expression of a functional protein that would perform the normal functionality in a wild-type organism. In one embodiment, a gene may be disrupted by introduction of one or more deletion, addition (insertion), substitution mutations in its coding region or in its regulatory elements. In one particular embodiment, a gene is disrupted by introduction of one or more deletion, addition (insertion), substitution mutations in its coding region.

The terms "targeted disruption" or "targeted deletion" refer to disruption of the functionality of a gene or a coding region of a gene by introduction of at least one deletion, addition, substitution mutation at a specific location of the gene or coding region which results in a loss of function of the protein encoded by the mutated gene or mutated coding region.

It will be readily apparent to those skilled in the art that the systems and methods described herein may be modified and substitutions may be made using suitable equivalents without departing from the scope of the embodiments disclosed herein. Having now described certain embodiments in detail, the same will be more clearly understood by reference to the following examples, which are included for purposes of illustration only and are not intended to be limiting.

EXAMPLES

Example 1 Deletion of Specific Hfs Hydrogenase Subunits Increases Ethanol Production in *T. saccharolyticum*

The primary hydrogenase in *Thermoanaerobacterium. saccharolyticum* is called hfs, which has 4 subunits, hfsA, hfsB, hfsC and hfsD (FIG. 1). In this Example, specific subunit(s) of the Hfs gene in *Thermoanaerobacterium saccharolyticum* were disrupted to generate strains with higher ethanol yield.

Figure 2A:
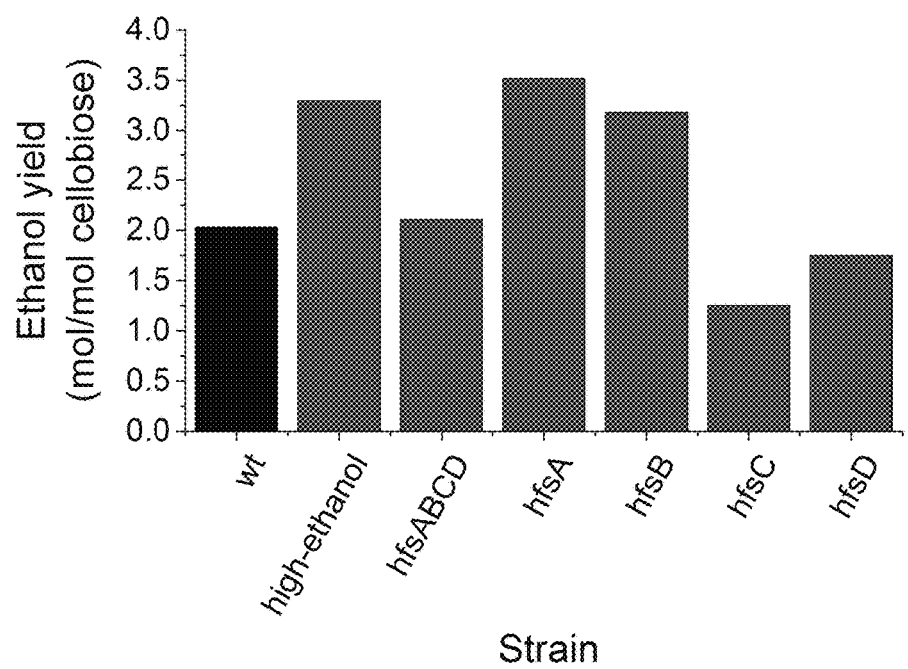
FIG. 2A shows ethanol yield by various hfs subunit deletion strains of *T. saccharolyticum*.
Figure 2B:
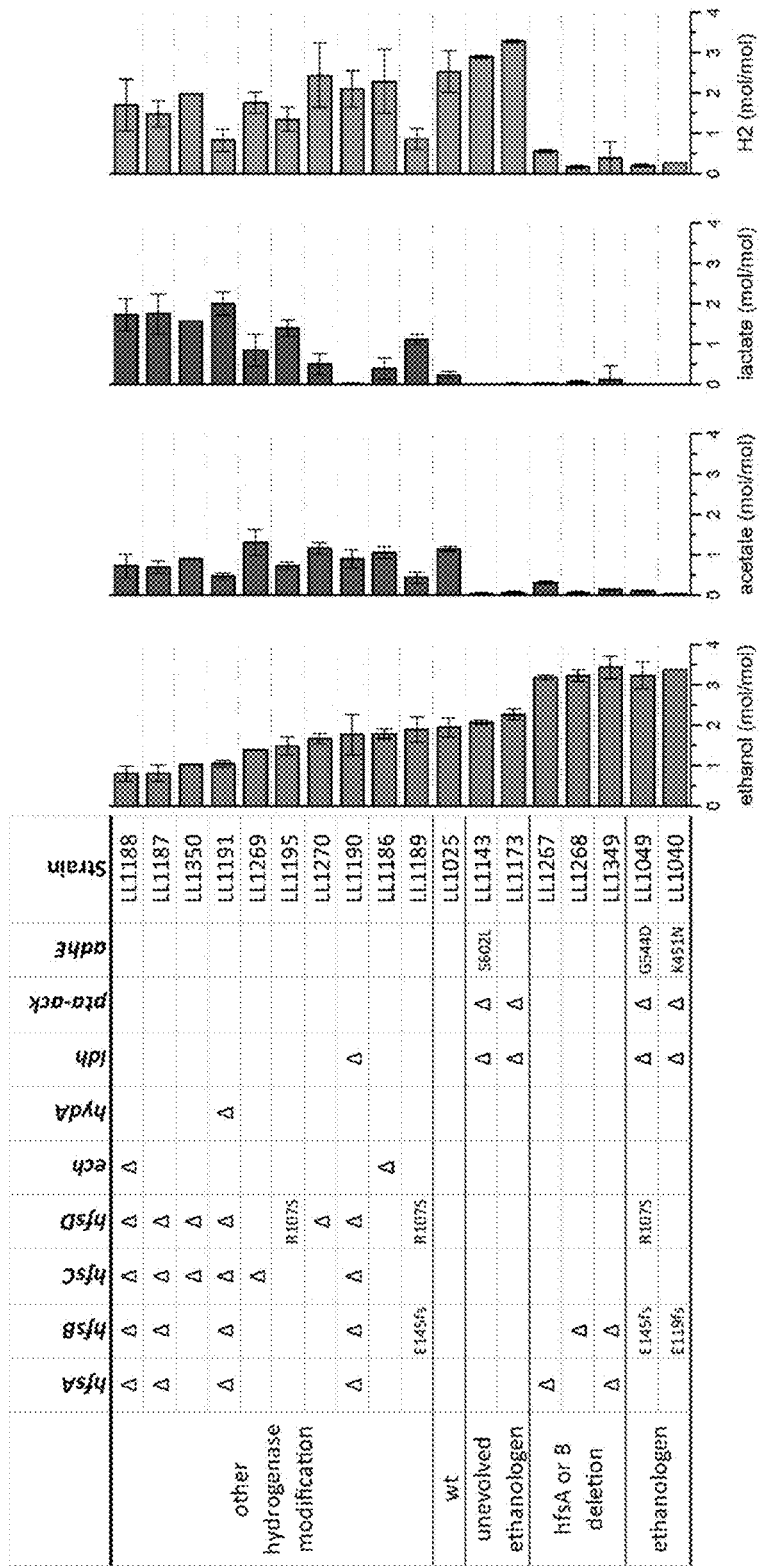
FIG. 2B shows fermentation data for strains of *Thermoanaerobacterium saccharolyticum* with various genetic modifications grown on 5 g/l cellobiose. The yield of ethanol, acetate, lactate and hydrogen (H2) are presented in units of mole product per mole cellobiose consumed. Where present, error bars represent one standard deviation, n≥2.

When either hfsA or hfsB was disrupted, but hfsC and hfsD were kept intact, ethanol production was similar to the high ethanol (ethanologen) strains (FIG. 2).

In order to understand the mechanism for increased ethanol production, the strains were analyzed by whole genome re-sequencing to identify secondary mutations, and by RNAseq to measure changes in gene expression. LC/MS-MS was also used to measure changes in protein abundance. adhE was found to be consistently over-expressed in the high ethanol producing strains, such as the HfsA and HfsB deletion strains. Significant (4-5×) upregulation of adhE at both gene and protein levels were observed in the hfsA or hfsB deletion strains. By contrast, hfs deletions of the other subunits have almost no effects on downstream gene expression.

Enzymatic assays were used to check for the possibility of regulatory effects. ADH, ALDH and FNOR activities were measured with both NADH and NADPH cofactors. High ADH-NADH specific activity was observed in ΔhfsB strain.

In summary, this Example shows the presence of a previously-unknown regulatory mechanism of the ethanol production pathway in *T saccharolyticum*. This experiment has also demonstrated a tool for rapid creation of ethanologen strains by deletion of hfsA or hfsB, which is sufficient to generate an ethanologen phenotype in *T. saccharolyticum* and other members of the genus.

Example 2 Deletion of Hfs Subunit B in Other Thermoanaerobacterium Strains

The improvement from hfsA or hfsB deletions is not limited to *T saccharolyticum*. Similar effects were also observed in two other organisms, *Thermoanaerobacterium thermosaccharolyticum* and *Thermoanaerobacterium xylanolyticum* (FIG. 3). In all 3 organisms, ethanol yield was greater than 80% of the theoretical maximum. The hfsB deletion strains performed almost as well as another engineered strains, M1442 (Δ(pta-ack) Δldh Δor795::metE-ure Δeps) on 20 g/l cellobiose (FIG. 4). (Note, strain M1442 is also described as strain LL1049 in FIG. 2B) This genetic modification is a quick way to generate high-ethanol-producing strains. These strains could be paired with cellulolytic strains (i.e. *C. thermocellum*) to convert plant biomass into ethanol.

Materials and Methods

Media and Growth Conditions. Genetic modifications of *T. saccharolyticum* JW/SL-YS485 strains were performed in CTFUD medium, containing 1.3 g/L $(NH_4)_2SO_4$, 1.5 g/L $KH_2PO_4$, 0.13 g/L $CaCl_2 \cdot 2H_2O$, 2.6 g/L $MgCl_2 \cdot 6H_2O$, 0.001 g/L $FeSO_4 \cdot 7H_2O$, 4.5 g/L yeast extract, 5 g/L cellobiose, 3 g/L sodium citrate tribasic dihydrate, 0.5 g/L L-cysteine-HCl monohydrate, 0.002 g/L resazurin and 10 g/L agarose (for solid media only). The pH was adjusted to 6.7 for selection with kanamycin (200 μg/ml), or pH was adjusted to 6.1 for selection with erythromycin (25 μg/ml).

Measurement of fermentation products and growth of T saccharolyticum were performed in MTC-6 medium [12], including 5 g/L cellobiose, 9.25 g/L MOPS (morpholinepropanesulfonic acid) sodium salt, 2 g/L ammonium chloride, 2 g/L potassium citrate monohydrate, 1.25 g/L citric acid monohydrate, 1 g/L $Na_2SO_4$, 1 g/L $KH_2PO_4$, 2.5 g/L $NaHCO_3$, 2 g/L urea, 1 g/L $MgCl_2 \cdot 6H_2O$, 0.2 g/L $CaCl_2 \cdot H_2O$, 0.1 g/L $FeCl_2 \cdot 6H_2O$, 1 g/L L-cysteine HCl monohydrate, 0.02 g/L pyridoxamine HCl, 0.004 g/L p-aminobenzoic acid (PABA), 0.004 g/L D-biotin, 0.002 g/L Vitamin B12, 0.04 g/L thiamine, 0.005 g/L $MnCl_2 \cdot 4H_2O$, 0.005 g/L $CoCl_2 \cdot 6H_2O$, 0.002 g/L $ZnCl_2$, 0.001 g/L $CuCl_2 \cdot 2H_2O$, 0.001 g/L $H_3BO_3$, 0.001 g/L $Na_2MoO_4 \cdot 2H_2O$, 0.001 g/L $NiCl_2 \cdot 6H_2O$. It was prepared by combining six sterile solutions with minor modification under nitrogen atmosphere as described before [11]. All of six solutions were sterilized through a 0.22 μm filter (Corning, #430517). A solution, concentrated 2.5-fold, contained cellobiose, MOPS sodium salt and distilled water. B Solution, concentrated 25-fold, contained potassium citrate monohydrate, citric acid monohydrate, $Na_2SO_4$, $KH_2PO_4$, $NaHCO_3$ and distilled water. C solution, concentrated 50-fold, contained ammonium chloride and distilled water. D solution, concentrated 50-fold, contained $MgCl_2 \cdot 6H_2O$, $CaCl_2 \cdot H_2O$, $FeCl_2 \cdot 6H_2O$, L-cysteine HCl monohydrate. E solution, concentrated 50-fold, contained thiamine, pyridoxamine HCl, p-aminobenzoic acid (PABA), D-biotin, Vitamin B12. F solution, concentrated 1000-fold, contained $MnCl_2 \cdot 4H_2O$, $CoCl_2 \cdot 6H_2O$, $ZnCl_2$, $CuCl_2 \cdot 2H_2O$, $H_3BO_3$, $Na_2MoO_4 \cdot 2H_2O$, $NiCl_2 \cdot 6H_2O$. For some fermentation required additional compositions, additional compositions were added after six solutions were combined. The pH was adjusted to 6.1 as the optimal pH for growth. Fermentations of *T. saccharolyticum* were done in 125-ml glass bottles at 55° C. under nitrogen atmosphere. The working volume is 50 ml with shaking at 250 rpm. Fermentations were allowed to proceed for 72 h at which point samples were collected for analysis.

*E. coli* strains used for cloning were grown aerobically at 37° C. in Lysogeny Broth (LB) [14] medium with either kanamycin (200 μg/ml) or erythromycin (25 μg/ml). For cultivation on solid medium, 15 g/L agarose was added.

All reagents used were from Sigma-Aldrich unless otherwise noted. All solutions were made with water purified using a MilliQ system (Millipore, Billerica, Mass.).

Plasmid Construction. Plasmids for gene deletion were designed as previously described [15] with either kanamycin or erythromycin resistance cassettes from plasmids pMU433 or pZJ23 flanked by 1.0 to 0.5-kb regions homologous to the 5' and 3' regions of the deletion target of interest. Plasmid pZJ23 was created as a new deletion vector by assembling an erythromycin cassette from the ALK2 strain and *E. coli* replication region from plasmid pUC19. Homologous regions of deletion targets of interest were amplified from wild type *T. saccharolyticum* (LL1025).

Plasmids were assembled by Gibson assembly master mix (New England Biolabs, Ipswich, Mass.). The assembled circular plasmids were transformed into *E. coli* DH5α chemical competent cells (New England Biolabs, Ipswich, Mass.) for propagation. Plasmids were purified by a Qiagen miniprep kit (Qiagen Inc., Germantown, Md.).

Transformation of *T. saccharolyticum*. Plasmids were transformed into naturally-competent *T. saccharolyticum* as described before [16, 17]. Mutant were grown and selected on solid medium with kanamycin (200 μg/ml) at 55° C. or with erythromycin (20 μg/ml) at 48° C. in an anaerobic chamber (COY Labs, Grass Lake, Mich.). Mutant colonies appeared on selection plates after about 3 days. Target gene deletions with chromosomal integration of both homology regions were confirmed by PCR with primers external to the target genes.

Preparation of Cell-Free Extracts. *T. saccharolyticum* cells were grown in CTFUD medium in an anaerobic chamber (COY labs, Grass Lake, Mich.), and harvested in the exponential phase of growth. To prepare cell-free extracts, cells were collected by centrifugation at 6000 g for 15 minutes and washed twice under similar conditions with a deoxygenated buffer containing 100 mM Tris-HCl (pH 7.5 at 0° C.) and 5 mM dithiothreitol (DTT). Cells were resuspended in 3 ml of the washing buffer. Resuspended cells were lysed by adding $10^4$ U of Ready-lyse lysozyme solution (Epicentre, Madison, Wis.) and 50 U of DNase (Thermo scientific, Waltham, Mass.) and then incubated at room temperature for 20 minutes. The crude lysate was centrifuged at 12,000 g for 5 minutes and the supernatant was collected as cell-free extract. The total amount of protein in the extract was determined by Bradford assay, using bovine serum albumin as the standard.

Enzymes Assays. Enzyme activity was assayed in an anaerobic chamber (COY labs, Grass Lake, Mich.) using an Agilent 8453 spectrophotometer with Peltier temperature control module (part number 89090A) to maintain assay temperature. The reaction volume was 1 ml, in reduced-volume quartz cuvettes (part number 29MES10; Precision Cells Inc., NY) with a 1.0 cm path length. All enzyme activities are expressed as μmol of product·$min^{-1}$·(mg of cell extract protein)$^{-1}$. For each enzyme assay, at least two concentrations of cell extract were used to confirm that specific activity was proportional to the amount of extract added.

All chemicals and coupling enzymes were purchased from Sigma except for coenzyme A, which is from EMD Millipore (Billerica, Mass.). All chemicals were prepared fresh weekly.

Ferredoxin nicotinamide oxidoreductase (FNOR) was assayed by the reduction of benzyl viologen at 578 nm at 55° C. with minor modifications as described before in Lo, J. et al. Deletion of nfnAB in *Thermoanaerobacterium saccharolyticum* and its effect on metabolism. J. Bacteriol. 197, JB.00347-15 (2015). An extinction coefficient of $\xi_{578}$=7.8 $mM^{-1}$ $cm^{-1}$ was used for calculating activity. The assay mixture contained 100 mM Tris-HCl (pH=7.5 at 55° C.), 0.5 mM DTT, 1 mM benzyl viologen and cell extract. The reaction was started by adding 0.3 mM NADH or NADPH. Alcohol and aldehyde dehydrogenase activity (ADH and ALDH, respectively) were measured as described in Lo, J., Zheng, T., Hon, S., Olson, D. G. & Lynd, L. R. The bifunctional alcohol and aldehyde dehydrogenase gene, adhe, is necessary for ethanol production in *Clostridium thermocellum* and *Thermoanaerobacterium saccharolyticum*. J. Bacteriol. (in press), JB.02450-14 (2015). Briefly, the oxidation of NAD(P)H was followed by spectrophotometric observation at 340 nm ($\epsilon$=6,220$M^{-1}$ $cm^{-1}$). In all cases, the final assay volume was 0.8 ml. For the ADH (acetaldehyde reduction) reactions, the anaerobic reaction mixture contained 100 mM Tris-HCl buffer (pH 7.0), 5 mM FeSO4, 0.25 mM NAD(P)H, 18 mM acetaldehyde, 1 mM DTT, and cell extract as indicated. For the ALDH (acetyl-CoA reduction) reactions, the anaerobic reaction mixture contained 100 mM Tris-HCl buffer (pH 7.0), 5 uM FeSO4, 0.25 mM NAD(P)H, 1.25 mM acetyl-CoA, 1 mM DTT, and cell extract.

RNA Isolation, RT-PCR and qPCR for Determining Transcriptional Expression Level. 3 ml of bacterial culture was pelleted and lysed by digestion with lysozyme (15 mg/ml) and proteinase K (20 mg/ml). RNA was isolated with an RNeasy minikit (Qiagen Inc., Germantown, Md.) and digested with TURBO DNase (Life Technologies, Grand Island, N.Y.) to remove contaminating DNA. cDNA was synthesized from 500 ng of RNA using the iScript cDNA synthesis kit (Bio-Rad, Hercules, Calif.). Quantitative PCR (qPCR) was performed using cDNA with SsoFast EvaGreen Supermix (Bio-Rad, Hercules, Calif.) at an annealing temperature of 55° C. to determine expression levels of Tsac_0046, Tsac_0628 and Tsac_0629. In each case, expression was normalized to recA RNA levels. In order to confirm removal of contaminating DNA from RNA samples, cDNA was synthesized in the presence and absence of reverse transcriptase followed by qPCR using recA primers to insure only background levels were detected in the samples lacking reverse transcriptase. Standard curves were generated using a synthetic DNA template (gBlock, IDT, Coralville, Iowa) containing the amplicons.

Genomic Sequencing. Genomic DNA was submitted to the Joint Genome Institute (JGI) for sequencing with an Illumina MiSeq instrument. Paired-end reads were generated, with an average read length of 150 bp and paired distance of 500 bp. Raw data was analyzed using CLC Genomics Workbench, version 7.5 (Qiagen, USA). First reads were mapped to the reference genome (NC_017992). Mapping was improved by 2 rounds of local realignment. The CLC Probabilistic Variant Detection algorithm was used to determine small mutations (single and multiple nucleotide polymorphisms, short insertions and short deletions). Variants occurring in less than 90% of the reads and variants that were identical to those of the wild type strain (i.e. due to errors in the reference sequence) were filtered out. To determine larger mutations, the CLC InDel and Structural Variant algorithm was run. This tool analyzes unaligned ends of reads and annotates regions where a structural variation may have occurred, which are called breakpoints. Since the read length averaged 150 bp and the minimum mapping fraction was 0.5, a breakpoint can have up to 75 bp of sequence data. The resulting breakpoints were filtered to eliminate those with fewer than 10 reads or less than 20% "not perfectly matched." The breakpoint sequence was searched with the Basic Local Alignment Search Tool (BLAST) algorithm for similarity to known sequences. Pairs of matching left and right breakpoints were considered evidence for structural variations such as transposon insertions and gene deletions.

Analytical Techniques. Fermentation products: cellobiose, glucose, acetate, lactate, formate, pyruvate, succinate, malate and ethanol were analyzed by a Waters (Milford, Mass.) high pressure liquid chromatography (HPLC) system with an Aminex HPX-87H column (Bio-Rad, Hercules, Calif.). The column was eluted at 60° C. with 0.25 g/L $H_2SO_4$ at a flow rate of 0.6 ml/min Cellobiose, glucose, acetate, lactate, formate, succinate, malate and ethanol were detected by a Waters 410 refractive-index detector and pyruvate was detected by a Waters 2487 UV detector. Sample collection and processing were as reported previously.

Carbon from cell pellets were determined by elemental analysis with a TOC-V CPH and TNM-I analyzer (Shimadzu, Kyoto, Japan) operated by TOC-Control V software. Fermentation samples were prepared as described with small modifications [22]. A 1 ml sample was centrifuged to remove supernatant at 21,130×g for 5 minutes at room temperature. The cell pellet was washed twice with MilliQ water. After washing, the pellet was resuspended in a TOCN 25 ml glass vial containing 19.5 ml MilliQ water. The vials were then analyzed by the TOC-V CPH and TNM-I analyzer.

Hydrogen was determined by gas chromatography using a Model 310 SRI Instruments (Torrence, Calif.) gas chromatograph with a HayeSep D packed column using a thermal conductivity detector and nitrogen carrier gas. The nitrogen flow rate was 8.2 ml/min.

Example 3 Deletion of Hfs Subunit in Other Bacterial Species

To determine if the hfsB regulation system is present in other organisms, hfsB was deleted in *Clostridium thermocellum*, *Thermoanaerobacter mathranii*, *Thermoanaerobacterium xylanolyticum* and *Thermoanaerobacterium thermosaccharolyticum* (FIG. 6). In all of these organisms, ethanol production increased as a result of the disruption. In *C. thermocellum*, we made a deletion of the whole hfs operon (Clo1313_1796 to 1793) in addition to the deletion of just the hfsB subunit. In this organism, a pattern similar to that of *T. saccharolyticum*: deletion of the hfsB subunit alone that improved ethanol production was observed, whereas deletion of the whole hfs operon did not.

Strains used in this work were re-sequenced to confirm that the genetic modification had been made as intended, to check for possible contamination and to identify the presence of secondary mutations. All strains were correct, no evidence of contamination was found.

The contents of all cited references (including literature references, patents, patent applications, and websites) that may be cited throughout this application or listed below are hereby expressly incorporated by reference in their entirety for any purpose into the present disclosure. The disclosure may employ, unless otherwise indicated, conventional techniques of microbiology, molecular biology and cell biology, which are well known in the art.

The disclosed methods and systems may be modified without departing from the scope hereof. It should be noted that the matter contained in the above description or shown in the accompanying drawings should be interpreted as illustrative and not in a limiting sense.

LIST OF REFERENCES

The following references, patents and publication of patent applications are either cited in this disclosure or are of relevance to the present disclosure. All documents listed below, along with other papers, patents and publication of patent applications cited throughout this disclosures, are hereby incorporated by reference as if the full contents are reproduced herein.

Shaw, A Joe, David A Hogsett, and Lee R Lynd. 2009. "Identification of the [FeFe]-Hydrogenase Responsible for Hydrogen Generation in *Thermoanaerobacterium Saccharolyticum* and Demonstration of Increased Ethanol Yield via Hydrogenase Knockout." Journal of Bacteriology 191 (20) (October): 6457-64. doi: 10.1128/JB.00497-09.

Shaw, A Joe, Bethany B Miller, Stephen R Rogers, William R Kenealy, Alex Meola, Ashwini Bhandiwad, W Ryan Sillers, Indraneel Shikhare, David A Hogsett, and Christopher D Herring. 2015. "Anaerobic Detoxification of Acetic Acid in a Thermophilic Ethanologen." Biotechnology for Biofuels 8:75. doi:10.1186/s13068-015-0257-4.

Shaw, a J., Covalla, S. F., Hogsett, D. A. & Herring, C. D. Marker removal system for *Thermoanaerobacterium saccharolyticum* and development of a markerless ethanologen. Appl. Environ. Microbiol. 77, 2534-6 (2011).

Mai, V., Lorenz, W. W. & Wiegel, J. Transformation of *Thermoanaerobacterium* sp. strain JW/SL-Y5485 with plasmid pIKM1 conferring kanamycin resistance. FEMS Microbiol. Lett. 148, 163-167 (1997).

Shaw, A. J., Hogsett, D. A. & Lynd, L. R. Natural competence in *Thermoanaerobacter* and *Thermoanaerobacterium* species. Appl. Environ. Microbiol. 76, 4713-4719 (2010).

Lynd L R, Weimer P J, van Zyl W H, Pretorius I S. 2002. Microbial cellulose utilization: fundamentals and biotechnology. Microbiol. Mol. Biol. Rev. 66:506-577.

Blumer-Schuette S E, Brown S D, Sander K B, Bayer E A, Kataeva I, Zurawski J V, Conway J M, Adams M W W, Kelly R M. 2014. Thermophilic lignocellulose deconstruction. FEMS Microbiol. Rev. 38:393-448.

Mai V, Lorenz W W, Wiegel J. 1997. Transformation of *Thermoanaerobacterium* sp. strain JW/SL-Y5485 with plasmid pIKM1 conferring kanamycin resistance. FEMS Microbiol. Lett. 148:163-167.

Shaw A J, Covalla S F, Miller B B, Firliet B T, Hogsett D A, Herring C D. 2012. Urease expression in a *Thermoanaerobacterium saccharolyticum* ethanologen allows high titer ethanol production. Metab. Eng. 14:528-532.

Shao X J, Raman B, Zhu M J, Mielenz J R, Brown S D, Guss A M, Lynd L R. 2011. Mutant selection and phenotypic and genetic characterization of ethanol-tolerant strains of *Clostridium thermocellum*. Appl. Microbiol. Biotechnol. 92:641-652.

Williams T I, Combs J C, Lynn B C, Strobel H J. 2007. Proteomic profile changes in membranes of ethanol-tolerant *Clostridium thermocellum*. Appl. Microbiol. Biotechnol. 74:422-432.

Sudha Rani K, Swamy M, Sunitha D, Haritha D, Seenayya G. 1996. Improved ethanol tolerance and production in strains of *Clostridium thermocellum*. World J. Microbiol. Biotechnol. 12:57-60.

Sato K, Tomita M, Yonermura S, Goto S, Sekine K, Okuma E, Takagi Y, Hon-nami K, Saiki T. 1993. Characterization of and ethanol hyper-production by *Clostridium thermocellum* I-1-B. Biosci. Biotechnol. Biochem. 57:2116-2121.

Argyros D A, Tripathi S A, Barrett T F, Rogers S R, Feinberg L F, Olson D G, Foden J M, Miller B B, Lynd L R, Hogsett D A, Caiazza N C. 2011. High ethanol titers from cellulose by using metabolically engineered thermophilic, anaerobic microbes. Appl. Environ. Microbiol. 77:8288-8294.

Shaw A J, Podkaminer K K, Desai S G, Bardsley J S, Rogers S R, Thorne P G, Hogsett D A, Lynd L R. 2008. Metabolic engineering of a thermophilic bacterium to produce ethanol at high yield. Proc. Natl. Acad. Sci. U.S.A. 105:13769-13774.

König S. 1998. Subunit structure, function and organisation of pyruvate decarboxylases from various organisms. Biochim Biophys. Acta 1385:271-286.

Extance J, Crennell S J, Eley K, Cripps R, Hough D W, Danson M J. 2013. Structure of a bifunctional alcohol dehydrogenase involved in bioethanol generation in *Geobacillus thermoglucosidasius*. Acta Crystallogr. Sect. D Biol. Crystallogr. 69:2104-2115.

Membrillo-Herna J, Echave P, Cabiscol E, Tamarit J, Ros J, Lin E C C. 2000. Evolution of the adhE gene product of *Escherichia coli* from a functional reductase to a dehydrogenase. J. Biol. Chem. 275:33869-33875.

Yao S. 2008. Ph.D. thesis. Technical University of Denmark, Denmark.

Peng H, Wu G, Shao W. 2008. The aldehyde/alcohol dehydrogenase (AdhE) in relation to the ethanol formation in *Thermoanaerobacter ethanolicus* JW200. Anaerobe 14:125-127.

Bhandiwad A, Shaw A J, Guss A, Guseva A, Bahl H, Lynd L R. 2014. Metabolic engineering of *Thermoanaerobacterium saccharolyticum* for n-butanol production. Metab. Eng. 21:17-25.

Pineda E, Encalada R, Olivos-Garcia A, Néquiz M, Moreno-Sanchez R, Saavedra E. 2013. The bifunctional aldehyde-alcohol dehydrogenase controls ethanol and acetate production in *Entamoeba histolytica* under aerobic conditions. FEBS Lett. 587:178-184.

Boxma B, Voncken F, Jannink S, van Alen T, Akhmanova A, van Weelden S W H, van Hellemond J J, Ricard G, Huynen M, Tielens A G M, Hackstein 2004. The anaerobic chytridiomycete fungus *Piromyces* sp. E2 produces ethanol via pyruvate:formate lyase and an alcohol dehydrogenase E. Mol. Microbiol. 51:1389-1399.

Atteia A, van Lis R, Mendoza-Hernández G, Henze K, Martin W, Riveros-Rosas H, González-Halphen D. 2003. Bifunctional aldehyde/alcohol dehydrogenase (ADHE) in chlorophyte algal mitochondria. Plant Mol. Biol. 53:175-188.

Lo J, Zheng T, Hon S, Olson D G, Lynd L R. 2015. The bifunctional alcohol and aldehyde dehydrogenase gene, adhE, is necessary for ethanol production in *Clostridium thermocellum* and *Thermoanaerobacterium saccharolyticum*. J. Bacteriol. JB02450-14.

Brown S D, Guss A M, Karpinets T V, Parks J M, Smolin N, Yang S, Land M L, Klingeman D M, Bhandiwad A, Rodriguez Jr. M, Raman B, Shao X, Mielenz J R, Smith J C, Keller M, Lynd L R. 2011. Mutant alcohol dehydrogenase leads to improved ethanol tolerance in *Clostridium thermocellum*. Proc. Natl. Acad. Sci. 108: 13752-13757.

Olson D G, Lynd L R. 2012. Transformation of *Clostridium thermocellum* by electroporation. Methods in Enzymology, 1st ed. Elsevier Inc.

Shaw A J, Hogsett D A, Lynd L R. 2010. Natural competence in *Thermoanaerobacter* and *Thermoanaerobacterium* species. Appl. Environ. Microbiol. 76:4713-4719.

Zhou J, Olson D G, Argyros D A, Deng Y, van Gulik W M, van Dijken J P, Lynd L R. 2013. Atypical glycolysis in *Clostridium thermocellum*. Appl. Environ. Microbiol. 79:3000-3008.

Zhang Y, Lynd L R. 2003. Quantification of cell and cellulase mass concentrations during anaerobic cellulose fermentation: development of an enzyme-linked immunosorbent assay-based method with application to *Clostridium thermocellum* batch cultures. Anal. Chem. 75:3131-3139.

Espinosa A, Yan L, Zhang Z, Foster L, Clark D, Li E, Stanley Jr. S L. 2001. The bifunctional *Entamoeba histolytica* alcohol dehydrogenase 2 (EhADH2) protein is necessary for amebic growth and survival and requires an intact C-terminal domain for both alcohol dehydrogenase and acetaldehyde dehydrogenase activity. J. Biol. Chem. 276:20136-20143.

Schwarzenbacher R, von Delft F, Canaves J M, Brinen L S, Dai X, Deacon A M, Elsliger M A, Eshaghi S, Floyd R, Godzik A, Grittini C, Grzechnik S K, Guda C, Jaroszewski L, Karlak C, Klock H E, Koesema E, Kovarik J S, Kreusch A, Kuhn P, Lesley S A, Mcmullan D, Mcphillips T M, Miller M A, Miller M D, Morse A, Moy K, Ouyang J, Page R, Robb A, Rodrigues K, Selby T L, Spraggon G, Stevens R C, van den Bedem H, Velasquez J, Vincent J, Wang X, West B, Wolf G, Hodgson K O, Wooley J, Wilson I A. 2004. Crystal structure of an iron-containing 1,3-propanediol dehydrogenase (TM0920) from *Thermotoga maritima* at 1.3 Å resolution. PROTEINS Struct. Funct. Bioinforma. 54:174-177.

Jorgensen W L, Chandrasekhar J, Madura J D, Impey R W, Klein M L. 1983. Comparison of simple potential functions for simulating liquid water. J. Chem. Phys. 79:926-935.

Jo S, Kim T, Iyer V G, Im W. 2008. Software news and updates CHARMM-GUI: A web-based graphical user interface for CHARMM. J. Comput. Chem. 29:1859-1865.

Koukos P I, Glykos N M. 2013. Grcarma: A fully automated task-oriented interface for the analysis of molecular dynamics trajectories. J. Comput. Chem. 34:2310-2312.

Yao S, Mikkelsen M J. 2010. Identification and overexpression of a bifunctional aldehyde/alcohol dehydrogenase responsible for ethanol production in *Thermoanaerobacter mathranii*. J. Mol. Microbiol. Biotechnol. 19:123-133.

Dailly Y, Bunch P, Clark D. 2000. Comparison of the fermentative alcohol dehydrogenases of *Salmonella typhimurium* and *Escherichia coli*. Microbios 103:179-196.

Pei J, Zhou Q, Jiang Y, Le Y, Li H, Shao W, Wiegel J. 2010. *Thermoanaerobacter* spp. control ethanol pathway via transcriptional regulation and versatility of key enzymes. Metab. Eng. 12:420-428.

Arnau J, Jorgensen F, Madsen S M, Vrang A, Israelsen H. 1998. Cloning of the *Lactococcus lactis* adhE gene, encoding a multifunctional alcohol dehydrogenase, by complementation of a fermentative mutant of *Escherichia coli*. J. Bacteriol. 180:3049-3055.

Bruchhaus I, Tannich E. 1994. Purification and molecular characterization of the NAD(+)-dependent acetaldehyde/alcohol dehydrogenase from *Entamoeba histolytica*. Biochem. J. 303:743-748.

Koo O K, Jeong D W, Lee J M, Kim M J, Lee J H, Chang H C, Kim J H, Lee H J. 2005. Cloning and characterization of the bifunctional alcohol/acetaldehyde dehydrogenase gene (adhE) in *Leuconostoc mesenteroides* isolated from kimchi. Biotechnol. Lett. 27:505-510.

Chen M, Li E, Stanley S L. 2004. Structural analysis of the acetaldehyde dehydrogenase activity of *Entamoeba histolytica* alcohol dehydrogenase 2 (EhADH2), a member of the ADHE enzyme family Mol. Biochem. Parasitol. 137:201-205.

Montella C, Bellsolell L, Perez-Luque R, Badia J, Baldoma L, Coll M, Aguilar J. 2005. Crystal structure of an iron-dependent group III dehydrogenase that interconverts L-lactaldehyde and L-1,2-propanediol in *Escherichia coli*. J. Bacteriol. 187:4957-4966.

Huang H, Wang S, Moll J, Thauer R K. 2012. Electron bifurcation involved in the energy metabolism of the acetogenic bacterium *Moorella thermoacetica* growing on glucose or H2 plus CO2. J. Bacteriol. 194:3689-3699.

Currie D H, Guss A M, Herring C D, Giannone R J, Johnson C M, Lankford P K, Brown S D, Hettich R L, Lynd L R. 2014. Profile of secreted hydrolases, associated proteins, and SlpA in *Thermoanaerobacterium saccharolyticum* during the degradation of hemicellulose. Appl. Environ. Microbiol. 80:5001-5011.

Verbeke T J, Zhang X, Henrissat B, Spicer V, Rydzak T, Krokhin O V., Fristensky B, Levin D B, Sparling R. 2013. Genomic evaluation of *Thermoanaerobacter* spp. for the construction of designer co-cultures to improve lignocellulosic biofuel production. PLoS One 8:1-18.

Radianingtyas H, Wright P C. 2003. Alcohol dehydrogenases from thermophilic and hyperthermophilic archaea and bacteria. FEMS Microbiol. Rev. 27:593-616.

Burdette D, Zeikus J G. 1994. Purification of acetaldehyde dehydrogenase and alcohol dehydrogenases from *Thermoanaerobacter ethanolicus* 39E and characterization of the secondary-alcohol dehydrogenase (20 Adh) as a bifunctional alcohol dehydrogenase-acetyl-CoA reductive thioesterase. Biochem. J. 302:163-170.

Lamed R, Zeikus J G. 1980 Ethanol production by thermophilic bacteria: relationship between fermentation product yields of and catabolic enzyme activities in *Clostridium thermocellum* and *Thermoanaerobium brockii*. J. Bacteriol. 144:569-578.

Neale A D, Scopes R K, Kelly J M, Wettenhall R E H. 1986. The two alcohol dehydrogenases of *Zymomonas mobilis* purification by differential dye ligand chromatography, molecular characterisation and physiological roles. Eur. J. Biochem. 154:119-124.

Chen Z, Lee W R, Chang S H. 1991. Role of aspartic acid 38 in the cofactor specificity of *Drosophila* alcohol dehydrogenase. Eur. J. Biochem. 202:263-267.

Kessler D, Herth W, Knappe J. 1992. Ultrastructure and pyruvate formate-lyase radical quenching property of the multienzymic AdhE protein of *Escherichia coli*. J. Biol. Chem. 267:18073-18073.

Biswas R, Zheng T, Olson D G, Lynd L R, Guss A M. 2015. Elimination of hydrogenase active site assembly blocks H2 production and increases ethanol yield in *Clostridium thermocellum*. Biotechnol. Biofuels. In press.

Wyman C E. 2007. What is (and is not) vital to advancing cellulosic ethanol. Trends Biotechnol. 25:153-157.

Olson D G, McBride J E, Shaw A J, Lynd L R, Joe Shaw A. 2012. Recent progress in consolidated bioprocessing. Curr. Opin. Biotechnol. 23:396-405.

Shaw A J, Podkaminer K K, Desai S G, Bardsley J S, Rogers S R, Thorne P G, Hogsett D A, Lynd L R. 2008. Metabolic engineering of a thermophilic bacterium to produce ethanol at high yield. Proc. Natl. Acad. Sci. U.S.A. 105:13769-13774.

Shaw J A, Jenney F E, Adams M W W, Lynd L R. 2008. End-product pathways in the xylose fermenting bacterium, *Thermoanaerobacterium saccharolyticum*. Enzyme Microb. Technol. 42:453-458.

Lo J, Zheng T, Hon S, Olson D G, Lynd L R. 2015. The bifunctional alcohol and aldehyde dehydrogenase gene, adhE, is necessary for ethanol production in *Clostridium thermocellum* and *Thermoanaerobacterium saccharolyticum*. J. Bacteriol. 197:1386-1393.

Wang S, Huang H, Moll J, Thauer R K. 2010. NADP+ reduction with reduced ferredoxin and NADP+ reduction with NADH are coupled via an electron-bifurcating enzyme complex in *Clostridium kluyveri*. J. Bacteriol. 192:5115-23.

Buckel W, Thauer R K. 2013. Energy conservation via electron bifurcating ferredoxin reduction and proton/Na(+) translocating ferredoxin oxidation. Biochim Biophys. Acta 1827:94-113.

Tripathi S A, Olson D G, Argyros D A, Miller B B, Barrett T F, Murphy D M, McCool J D, Warner A K, Rajgarhia V B, Lynd L R, Hogsett D A, Caiazza N C. 2010. Development of pyrF-based genetic system for targeted gene deletion in *Clostridium thermocellum* and creation of a pta mutant. Appl. Environ. Microbiol. 76:6591-6599.

Shanks R M Q, Caiazza N C, Hinsa S M, Toutain C M, O'Toole G A. 2006. *Saccharomyces cerevisiae*-based molecular tool kit for manipulation of genes from gram-negative bacteria. Appl. Environ. Microbiol. 72:5027-5036.

Shaw a J, Hogsett D a, Lynd L R. 2009. Identification of the [FeFe]-hydrogenase responsible for hydrogen generation in *Thermoanaerobacterium saccharolyticum* and demonstration of increased ethanol yield via hydrogenase knockout. J. Bacteriol. 191:6457-64.

Zhou J, Olson D G, Argyros D A, Deng Y, van Gulik W M, van Dijken J P, Lynd L R. 2013. Atypical glycolysis in *Clostridium thermocellum*. Appl. Environ. Microbiol. 79:3000-8.

Fournier M, Dermoun Z, Durand M-C, Dolla A. 2004. A new function of the *Desulfovibrio vulgaris* Hildenborough [Fe] hydrogenase in the protection against oxidative stress. J. Biol. Chem. 279:1787-93.

Lamed R, Zeikus J G. 1980 Ethanol production by thermophilic bacteria: relationship between fermentation product yields of and catabolic enzyme activities in *Clostridium thermocellum* and *Thermoanaerobium brockii*. J. Bacteriol. 144:569-78.

Thorsness P E, Koshland D E. 1987. Inactivation of isocitrate dehydrogenase by phosphorylation is mediated by the negative charge of the phosphate. J. Biol. Chem. 262:10422-10425.

Van der Veen D, Lo J, Brown S D, Johnson C M, Tschaplinski T J, Martin M, Engle N L, van den Berg R a, Argyros A D, Caiazza N C, Guss A M, Lynd L R. 2013. Characterization of *Clostridium thermocellum* strains with disrupted fermentation end-product pathways. J. Ind. Microbiol. Biotechnol. 40:725-34.

Shaw a J, Covalla S F, Hogsett D a, Herring C D. 2011. Marker removal system for *Thermoanaerobacterium saccharolyticum* and development of a markerless ethanologen. Appl. Environ. Microbiol. 77:2534-6.

Lee J M, Venditti R A, Jameel H, Kenealy W R. 2011. Detoxification of woody hydrolyzates with activated carbon for bioconversion to ethanol by the thermophilic anaerobic bacterium *Thermoanaerobacterium saccharolyticum*. Biomass and Bioenergy 35:626-636.

Currie D H, Herring C D, Guss A M, Olson D G, Hogsett D a, Lynd L R. 2013. Functional heterologous expression of an engineered full length CipA from *Clostridium thermocellum* in *Thermoanaerobacterium saccharolyticum*. Biotechnol. Biofuels 6:32.

Biswas R, Zheng T, Olson D G, Lynd L R, Guss A M. 2015. Elimination of hydrogenase active site assembly blocks H2 production and increases ethanol yield in *Clostridium thermocellum*. Biotechnol. Biofuels 8:20.

Brown S D, Guss A M, Karpinets T V, Parks J M, Smolin N, Yang S, Land M L, Klingeman D M, Bhandiwad A, Rodriguez M, Raman B, Shao X, Mielenz J R, Smith J C, Keller M, Lynd L R. 2011. Mutant alcohol dehydrogenase leads to improved ethanol tolerance in *Clostridium thermocellum*. Proc. Natl. Acad. Sci. U.S.A. 108:13752-7.

Currie D H, Guss A M, Herring C D, Giannone R J, Johnson C M, Lankford P K, Brown S D, Hettich R L, Lynd L R. 2014. Profile of secreted hydrolases, associated proteins, and SlpA in *Thermoanaerobacterium saccharolyticum* during the degradation of hemicellulose. Appl. Environ. Microbiol. 80:5001-11.

Yao S, Mikkelsen M J. 2010. Metabolic engineering to improve ethanol production in *Thermoanaerobacter mathranii*. Appl. Microbiol. Biotechnol. 88:199-208.

Wiegel J, Ljungdahl L G. 1981. *Thermoanaerobacter ethanolicus* gen. nov., spec. nov., a new, extreme thermophilic, anaerobic bacterium. Arch. Microbiol. 128:343-348.

Burdette D, Zeikus J G. 1994. Purification of acetaldehyde dehydrogenase and alcohol dehydrogenases from *Thermoanaerobacter* ethanolicus 39E and characterization of the secondary-alcohol dehydrogenase (2 degrees Adh) as a bifunctional alcohol dehydrogenase—acetyl-CoA reductive thioest. Biochem. J. 302:163-70.

Yao S, Mikkelsen M J. 2010. Identification and overexpression of a bifunctional aldehyde/alcohol dehydrogenase responsible for ethanol production in *Thermoanaerobacter mathranii*. J. Mol. Microbiol. Biotechnol. 19:123-133.

Bryant F O, Wiegel J, Ljungdahl L G. 1988. Purification and Properties of Primary and Secondary Alcohol Dehydrogenases from *Thermoanaerobacter* ethanolicus. Appl. Environ. Microbiol. 54:460-465.

Lovitt R W, Shen G J, Zeikus J G. 1988. Ethanol production by thermophilic bacteria: biochemical basis for ethanol and hydrogen tolerance in *Clostridium thermohydrosulfuricum*. J. Bacteriol. 170:2809-15.

Lovitt R W, Longin R, Zeikus J G. 1984 Ethanol Production by Thermophilic Bacteria: Physiological Comparison of Solvent Effects on Parent and Alcohol-Tolerant Strains of *Clostridium thermohydrosulfuricum*. Appl. Envir. Microbiol. 48:171-177.

Carere C R, Rydzak T, Verbeke T J, Cicek N, Levin D B, Sparling R. 2012. Linking genome content to biofuel production yields: a meta-analysis of major catabolic pathways among select H2 and ethanol-producing bacteria. BMC Microbiol. 12:295.

Soboh B, Linder D, Hedderich R. 2004. A multisubunit membrane-bound [NiFe] hydrogenase and an NADH-dependent Fe-only hydrogenase in the fermenting bacterium *Thermoanaerobacter tengcongensis*. Microbiology 150:2451-63.

Amador-Noguez D, Feng X-J, Fan J, Roquet N, Rabitz H, Rabinowitz J D. 2010. Systems-level metabolic flux profiling elucidates a complete, bifurcated tricarboxylic acid cycle in *Clostridium acetobutylicum*. J. Bacteriol. 192:4452-61.

Lee Y-E, Jain M K, Lee C, Zeikus J G: Taxonomic Distinction of Saccharolytic Thermophilic Anaerobes: Description of *Thermoanaerobacterium xylanolyticum* gen. nov., sp. nov., and *Thermoanaerobacterium saccharolyticum* gen. nov., sp. nov.; Reclassification of *Thermoanaerobium brockii, Clostridium*. Int J Syst Bacteriol 1993, 43:41-51.

Shaw A J, Podkaminer K, Desai S, Bardsley J, Rogers S, Thorne P, Hogsett D A, Lynd L R: Metabolic engineering of a thermophilic bacterium to produce ethanol at high yield. Proc Natl Acad Sci USA 2008, 105:13769-13774.

Shaw A J, Covalla S F, Miller B B, Firliet B T, Hogsett D A, Herring C D: Urease expression in a *Thermoanaerobacterium saccharolyticum* ethanologen allows high titer ethanol production. Metab Eng 2012, 14:528-32.

Herring C D, Kenealy W R, Shaw A J, Raman B, Tschaplinski T J, Brown S D, Davison B H, Covalla S F, Sillers W R, Xu H, Tsakraklides V, Hogsett D A: Final Report on Development of *Thermoanaerobacterium Saccharolyticum* for the Conversion of Lignocellulose to Ethanol. Golden, Colo. (United States); 2012.

Lynd L R, Weimer P J, van Zyl W H, Pretorius I S: Microbial cellulose utilization: fundamentals and biotechnology. Microbiol Mol Biol Rev 2002, 66:506-577.

Lynd L R, van Zyl W H, McBride J E, Laser M: Consolidated bioprocessing of cellulosic biomass: an update. Curr Opin Biotechnol 2005, 16:577-583.

Shaw A J, Jenney Jr F E, Adams M W W, Lynd L R: End-product pathways in the xylose fermenting bacterium, *Thermoanaerobacterium saccharolyticum*. Enzyme Microb Technol 2008, 42:453-458.

Kanehisa M, Goto S: KEGG: Kyoto Encyclopedia of Genes and Genomes. 2000, 28:27-30.

Kanehisa M, Goto S, Sato Y, Kawashima M, Furumichi M, Tanabe M: Data, information, knowledge and principle: back to metabolism in KEGG. Nucleic Acids Res 2014, 42(Database issue):D199-205.

Chabriere E, Cavazza C, Contreras-Martel C, Fontecilla-Camps J C: Pyruvate-ferredoxin oxidoreductase. In Encyclopedia of Inorganic and Bioinorganic Chemistry; 2011:1-13.

Zhou J, Olson D G, Argyros D, Deng Y, van Gulik W, van Dijken J, Lynd L R: Atypical glycolysis in *Clostridium thermocellum*. Appl Environ Microbiol 2013, 79:3000-3008.

Hogsett D A: Cellulose hydrolysis and fermentation by *Clostridium thermocellum* for the production of ethanol Dartmouth College, Hanover, N.H.; 1995.

Olson D G, Lynd L R: Computational design and characterization of a temperature-sensitive plasmid replicon for gram positive thermophiles. J Biol Eng 2012, 6:5.

Bertani G: Studies on lysogenesis. I. The mode of phage liberation by lysogenic *Escherichia coli*. J Bacteriol 1951, 62:293-300.

Desai S G, Guerinot M L, Lynd L R: Cloning of L-lactate dehydrogenase and elimination of lactic acid production via gene knockout in *Thermoanaerobacterium saccharolyticum* JW/SL-YS485. Appl Microbiol Biotechnol 2004, 65:600-5.

Shaw A J, Hogsett D A, Lynd L R: Natural competence in *Thermoanaerobacter* and *Thermoanaerobacterium* species. Appl Environ Microbiol 2010, 76:4713-9.

Shaw A J, Hogsett D A, Lynd L R: Identification of the [FeFe]-hydrogenase responsible for hydrogen generation in *Thermoanaerobacterium saccharolyticum* and demonstration of increased ethanol yield via hydrogenase knockout. J Bacteriol 2009, 191:6457-64.

Kruger N: The Bradford method for protein quantitation. Methods Mol Biol 1994, 32:9-15.

Ma K, Adams M W.: Ferredoxin:NADP oxidoreductase from *Pyrococcus furiosus*. In Methods in Enzymology. Volume 334. Elsevier; 2001:40-45. [Methods in Enzymology]

Altschul S F, Gish W, Miller W, Myers E W, Lipman D J: Basic local alignment search tool. J Mol Biol 1990, 215:403-10.

Zhang Y P, Lynd L R: Regulation of cellulase synthesis in batch and continuous cultures of *Clostridium thermocellum*. J Bacteriol 2005, 187:99-106.

Van der Veen D, Lo J, Brown S D, Johnson C M, Tschaplinski T J, Martin M, Engle N L, van den Berg R A, Argyros A D, Caiazza N C, Guss A M, Lynd L R: Characterization of *Clostridium thermocellum* strains with disrupted fermentation end-product pathways. J Ind Microbiol Biotechnol 2013, 40:725-34.

Currie D H, Guss A M, Herring C D, Giannone R J, Johnson C M, Lankford P K, Brown S D, Hettich R L, Lynd L R: Profile of secreted hydrolases, associated proteins, and SlpA in *Thermoanaerobacterium saccharolyticum* during the degradation of hemicellulose. Appl Environ Microbiol 2014, 80:5001-11.

Ma K, Hutchins A, Sung S J, Adams M W: Pyruvate ferredoxin oxidoreductase from the hyperthermophilic archaeon, *Pyrococcus furiosus*, functions as a CoA-dependent pyruvate decarboxylase. Proc Natl Acad Sci USA 1997, 94:9608-13.

Eram M S, Oduaran E, Ma K: The bifunctional pyruvate decarboxylase/pyruvate ferredoxin oxidoreductase from *Thermococcus guaymasensis*. Archaea 2014, 2014:349-379.

Thauer R K, Kirchniawy F H, Jungermann K A: Properties and Function of the Pyruvate-Formate-Lyase Reaction in Clostridiae. Eur J Biochem 1972, 27:282-290.

Zeikus J.: Metabolism of One-Carbon Compounds by Chemotrophic Anaerobes. In Advances in Microbial Physiology. Volume 24. Elsevier; 1983:215-299. [Advances in Microbial Physiology]

Amador-Noguez D, Feng X, Fan J, Roquet N, Rabitz H, Rabinowitz J D: Systems-level metabolic flux profiling elucidates a complete, bifurcated tricarboxylic acid cycle in *Clostridium acetobutylicum*. J Bacteriol 2010, 192:4452-61.

Cronan J E, Zhao X, Jiang Y: Function, Attachment and Synthesis of Lipoic Acid in *Escherichia Coli*. Volume 50. Elsevier Masson S A S; 2005.

Wigley D B, Gamblin S J, Turkenburg J P, Dodson E J, Piontek K, Muirhead H, Holbrook J J: Structure of a ternary complex of an allosteric lactate dehydrogenase from *Bacillus stearothermophilus* at 2.5 A resolution. J Mol Biol 1992, 223:317-35.

Mai V, Lorenz W W, Wiegel J: Transformation of *Thermoanaerobacterium* sp. strain JW/SL-YS485 with plasmid pIKM1 conferring kanamycin resistance. FEMS Microbiol Lett 1997, 148:163-167.

Podkaminer K K, Guss A M, Trajano H L, Hogsett D A, Lynd L R: Characterization of xylan utilization and discovery of a new endoxylanase in *Thermoanaerobacterium saccharolyticum* through targeted gene deletions. Appl Environ Microbiol 2012, 78:8441-7.

What is claimed is:

1. A genetically engineered microorganism comprising a functional hfsC protein subunit and a functional hfsD protein subunit of hfs hydrogenase, wherein expression of hfsA and hfsB protein subunits of the hfs hydrogenase is disrupted,
  wherein said microorganism is selected from the group consisting of *Thermoanaerobacterium* sp., *Thermoanaerobacter mathranii* and *Clostridium thermocellum*.

2. The microorganism of claim 1, wherein said microorganism is selected from the group consisting of *Thermoanaerobacterium saccharolyticum*, *Thermoanaerobacterium thermosaccharolyticum*, and *Thermoanaerobacterium xylanolyticum*.

3. The microorganism of claim 1, wherein said disruption of the protein subunits hfsA and hfsB of the hfs hydrogenase in said microorganism is by targeted mutation.

4. The microorganism of claim 1, wherein said microorganism has an ethanol yield greater than 80% of theoretical yield.

5. The microorganism of claim 1, wherein the pta and ack genes in said microorganism are identical to the pta and ack genes in a wildtype strain of the same species.

6. The microorganism of claim 1, wherein ldh the gene in the microorganism is identical to the ldh gene in a wildtype strain of the same species.

7. The microorganism of claim 1, wherein amino acid sequence of said hfsA protein subunit is at least 80% identical to a sequence selected from the group consisting of SEQ ID No. 1, SEQ ID No. 2 and SEQ ID No. 3.

8. The microorganism of claim 1, wherein amino acid sequence of said hfsB protein subunit is at least 80% identical to a sequence selected from the group consisting of SEQ ID No. 4, SEQ ID No. 5 and SEQ ID No. 6.

9. The microorganism of claim 1, wherein said functional hfsC protein subunit has an amino acid sequence identical to that of wild-type hfsC protein subunit in said microorganism, and wherein said functional hfsD protein subunit has an amino acid sequence identical to that of wild-type hfsD protein subunit in said microorganism.

10. A method of producing ethanol from biomass, comprising contacting the biomass with the genetically engineered microorganism of claim 1 to produce ethanol.

11. The method of claim 10, wherein the microorganism is co-cultured with *Clostridium thermocellum* to produce ethanol from the biomass, wherein the *Clostridium thermocellum* is genetically engineered.

12. A method of generating the genetically engineered microorganism of claim 1, comprising disrupting expression of at least the hfsA and hfsB protein subunits of the hfs hydrogenase, said hfsB protein subunit having an amino acid sequence at least 80% identical to a sequence selected from the group consisting of SEQ ID No. 4, SEQ ID No. 5 and SEQ ID No. 6, and said hfsA protein subunit having an amino acid sequence at least 80% identical to a sequence selected from the group consisting of SEQ ID No. 1, SEQ ID No. 2 and SEQ ID No. 3.

* * * * *

UNITED STATES PATENT AND TRADEMARK OFFICE
CERTIFICATE OF CORRECTION

| | |
|---|---|
| PATENT NO. | : 10,619,172 B2 |
| APPLICATION NO. | : 15/656665 |
| DATED | : April 14, 2020 |
| INVENTOR(S) | : Eminoglu et al. |

Page 1 of 1

It is certified that error appears in the above-identified patent and that said Letters Patent is hereby corrected as shown below:

On the Title Page

Item (72):
"Aysenur Eminoglu, Hanover, NH (US)"
Should read:
--Aysenur Eminoglu, Rize, Turkey--

Signed and Sealed this
Ninth Day of June, 2020

Andrei Iancu
*Director of the United States Patent and Trademark Office*